US012236587B2

(12) United States Patent
Dhatt et al.

(10) Patent No.: US 12,236,587 B2
(45) Date of Patent: Feb. 25, 2025

(54) NEURAL NETWORK UTILIZATION WITH ULTRASOUND TECHNOLOGY

(71) Applicant: FUJIFILM SonoSite, Inc., Bothell, WA (US)

(72) Inventors: Davin Dhatt, Woodinville, WA (US); Thomas Duffy, Snohomish, WA (US); Adam Pely, Seattle, WA (US); Christopher White, North Vancouver (CA); Andrew Lundberg, Woodinville, WA (US); Paul Danset, Kirkland, WA (US); Craig Chamberlain, Seattle, WA (US); Diku Mandavia, Los Angeles, CA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 468 days.

(21) Appl. No.: 17/671,302

(22) Filed: Feb. 14, 2022

(65) Prior Publication Data
US 2023/0260107 A1 Aug. 17, 2023

(51) Int. Cl.
G06T 7/00 (2017.01)
G06N 5/04 (2023.01)
G16H 30/20 (2018.01)

(52) U.S. Cl.
CPC ............ *G06T 7/0012* (2013.01); *G06N 5/04* (2013.01); *G16H 30/20* (2018.01); G06T 2207/10132 (2013.01)

(58) Field of Classification Search
CPC ........ G06T 7/0012; G06T 2207/10132; G16H 30/20; G06N 5/04
See application file for complete search history.

(56) References Cited

U.S. PATENT DOCUMENTS 5,754,676 A * 5/1998 Komiya .................. G06F 18/21
382/170
8,483,432 B2 * 7/2013 Patwardhan .......... G06T 7/0012
382/209
(Continued)

FOREIGN PATENT DOCUMENTS

WO WO-2019166332 A1 * 9/2019 ........... A61B 8/4444
WO WO-2020089416 A1 * 5/2020 ........... A61B 8/0841

OTHER PUBLICATIONS

Jiang et al., 2010, "Medical image analysis with artificial neural networks" (pp. 617-631) (Year: 2010).*

Primary Examiner — Manav Seth
(74) Attorney, Agent, or Firm — Womble Bond Dickinson (US) LLP

(57) ABSTRACT

Examples herein include methods, systems, and computer program products for utilizing neural networks in ultrasound systems. The methods include processor(s) of a computing device identifying a neural network for implementation on the computing device to generate, based on ultrasound data, inferences and confidence levels for the inferences, the computing device being communicatively coupled via a computing network to an ultrasound machine configured to generate the ultrasound data. The processor(s) implements the neural network on the computing device, including configuring the neural network to generate an inference and a confidence level for at least one image of the images. The processor(s) obtains the ultrasound data including images from the ultrasound machine. The processor(s) determines, for the at least one image, an accuracy of the inference and the confidence level. The processor(s) automatically reconfigures the neural network to increase the accuracy based on the determining the accuracy.

13 Claims, 10 Drawing Sheets

(56) References Cited

U.S. PATENT DOCUMENTS

| | | | |
|---|---|---|---|
| 10,667,786 B2 * | 6/2020 | Peters | G06T 7/149 |
| 10,878,576 B2 * | 12/2020 | Han | G06T 7/174 |
| 11,151,721 B2 * | 10/2021 | Avendi | G06V 10/82 |
| 11,322,256 B2 * | 5/2022 | Sati | G16H 15/00 |
| 11,678,866 B2 * | 6/2023 | Dhatt | A61B 8/467 |
| | | | 600/437 |
| 12,122,053 B2 * | 10/2024 | Chen | G06N 3/08 |
| 12,133,770 B2 * | 11/2024 | White | A61B 8/5276 |
| 2004/0176689 A1 * | 9/2004 | Yamauchi | A61B 8/08 |
| | | | 600/450 |
| 2005/0114278 A1 * | 5/2005 | Saptharishi | G06N 3/082 |
| | | | 706/46 |
| 2021/0142177 A1 * | 5/2021 | Mallya | G06N 3/084 |
| 2021/0334955 A1 * | 10/2021 | Roth | G06T 7/0012 |
| 2021/0334975 A1 * | 10/2021 | Yang | G06V 10/28 |
| 2022/0059221 A1 * | 2/2022 | Zhu | G16H 50/80 |
| 2022/0130523 A1 * | 4/2022 | Wissel | G06N 20/00 |
| 2022/0138957 A1 * | 5/2022 | Xu | G06T 7/174 |
| | | | 382/157 |
| 2022/0142712 A1 * | 5/2022 | Toporek | G06N 3/082 |
| 2022/0237414 A1 * | 7/2022 | Zhang | A01M 21/00 |
| 2023/0033075 A1 * | 2/2023 | Xu | G06V 10/82 |
| 2023/0061998 A1 * | 3/2023 | Yang | G06N 3/08 |

* cited by examiner

NEURAL NETWORK UTILIZATION WITH ULTRASOUND TECHNOLOGY

BACKGROUND

Conventional ultrasound diagnostic imaging systems usually include a display screen to display ultrasound images during an ultrasound procedure. The display screens in various ultrasound systems include dedicated display screens and generic (off-the-shelf) display screens coupled to an ultrasound machine. Tablet computers are often utilized as an off-the-shelf display solution in ultrasound systems. These display screens are an important part of ultrasound diagnostic imaging systems because ultrasound systems generate ultrasound images by transmitting sound waves at frequencies above the audible spectrum into a body, receiving echo signals caused by the sound waves reflecting from internal body parts, and converting the echo signals into electrical signals for image generation. The display screens display these images to an operator and/or medical personnel who participate in treatment of patients.

The medical treatments and procedures that utilize ultrasound imaging are varied. Because ultrasound imaging is non-invasive, ultrasound systems are often used for imaging internal body parts in non-invasive medical procedures (e.g., inspecting a bladder volume). However, ultrasound systems can be used for assisting in invasive procedures, such as by visualizing a needle insertion. Both invasive and non-invasive procedures utilize ultrasound imaging systems with display screens.

Despite the known utility of display screens in ultrasound system, the utility of these screens in existing systems is limited. Conventional ultrasound systems most commonly include a single display screen, such as a tablet, coupled to an ultrasound machine. Utilizing a tablet as a monitor, a user of the ultrasound system can view ultrasound images during an ultrasound examination, but it may be difficult for additional personnel in the examination environment. Due to constraints in the medical environment in which the examination is being performed (e.g., space constraints, reflections from lighting, other environmental factors, etc.) medical personnel other than the ultrasound operator, including but not limited to, clinicians and nursing staff, may not have a vantage point from which to view ultrasound images on the tablet. But viewing these images would enable these personnel to provide valuable input to the operator of the ultrasound system. Unfortunately, personnel may opt not to view the images and provide this input, potentially compromising care, because attempts to view the display can create safety issues with the physical environment. For example, in attempting to gain better views, medical professionals may unintentionally create an unsafe or unsanitary condition during a medical procedure that utilizes an ultrasound system by adjusting their positions (e.g., moving closer to the tablet, leaning over or near a patient, etc.).

Some existing systems do provide multiple displays to allow for a larger audience in an examination room to view a procedure performed with an ultrasound system, but the additional displays do not provide medical personnel with the functionality of the initial display which is proximate to the operator. Content on these secondary displays is limited to a copy of the content on the primary display that is communicated over a one-way communication link from the ultrasound machine to the secondary display. Hence, the additional personnel are limited to viewing the content in the format provided by the ultrasound machine and are prevented from effecting changes. With these functionality limitations, the medical personnel may not be able to utilize the ultrasound images to their fullest potential, including in training situations.

SUMMARY

Shortcomings of the prior art are overcome, and additional advantages are provided through the provision of a method for utilizing one or more neural networks with an ultrasound system. The method includes, for example, program code executing on one or more processors of a computing device. The program code identifies a neural network for implementation on the computing device to generate, based on ultrasound data, inferences. The computing device is communicatively coupled, via a computing network, to an ultrasound machine. The ultrasound machine is configured to generate the ultrasound data. The program code obtains the ultrasound data, including images, from the ultrasound machine. The program code implements the neural network on the computing device, which includes implementing includes configuring the neural network to generate an inference for at least one image of the images. The program code determines, for the at least one image, an accuracy of the inference. The program code automatically reconfigures the neural network to increase the accuracy based on the program code determining the accuracy.

Shortcomings of the prior art are overcome, and additional advantages are provided by an ultrasound system for neural network utilization with ultrasound technology. The system includes an ultrasound machine. The ultrasound machine includes a clinical display including controls. The clinical display is configured to display ultrasound data; the ultrasound data includes images. The ultrasound data is obtained from an ultrasound probe communicatively coupled to the ultrasound machine. The ultrasound machine includes a communication device to transmit the ultrasound data to one or more computing devices via a communication link. The communication link couples the communication device of the ultrasound machine to the one or more computing devices. The system includes the one or more computing devices. The one or more computing devices include a memory, one or more neural networks accessible to one or more processors, the one or more processors in communication with the memory, a display in communication with the one or more processors, and program instructions stored on the memory that when executed by the one or more processors cause the one or more processors to perform various actions. For example, the program instructions, when executed, obtain, from the ultrasound machine, via the communication link, the ultrasound data. The program instructions, when executed, display the ultrasound data on the display screen, concurrently with displaying the ultrasound data on the clinical display. The program instructions, when executed, configure a neural network of the one or more neural networks to generate an inference for at least one image of the images. The program instructions, when executed, display, on the display with the ultrasound data, a visual indicator of the inference. The program instructions, when executed, obtain, via an interface of the one or more computing devices, a user input. The program instructions, when executed, transmit, via the communication link and to the ultrasound machine, the user input, a substance of the user input being automatically displayed on the clinical display upon receipt of the user input by the ultrasound machine based on a control of the controls of the clinical display being enabled.

Shortcomings of the prior art are overcome, and additional advantages are provided through the provision of a computer program product for neural network utilization with ultrasound technology. The computer program product comprises a computer readable storage medium readable by one or more processors of a computing device in a computing environment comprising an ultrasound system, the computer readable storage medium storing instructions that when executed by the one or more processors cause the one or more processors to perform various activities. For example, when executed, the instructions obtain from an ultrasound machine including a clinical display, wherein the ultrasound machine is communicatively coupled to the one or more processors, ultrasound data including images. The instructions, when executed, utilize a neural network configured on the computing device to provide an inference for at least one image of the images. The instructions, when executed, display, on a display of the computing device, concurrently with a display of the at least one image on the clinical display, the at least one image of the images, and the inference for the at least one image of the images. The instructions, when executed, obtain, via an interface of the computing device, during the displaying of the at least one image, an input. The instructions, when executed, transmit, via the communication link, to the ultrasound machine, the input, wherein the ultrasound machine effects a change based on obtaining the input.

Additional features are realized through the devices and techniques described herein. Other embodiments and aspects are described in detail herein and are considered a part of the claimed aspects.

BRIEF DESCRIPTION OF THE DRAWINGS

One or more aspects are particularly pointed out and distinctly claimed as examples in the claims at the conclusion of the specification. The foregoing and objects, features, and advantages of one or more aspects are apparent from the following detailed description taken in conjunction with the accompanying drawings in which:

DETAILED DESCRIPTION

Figure 1:
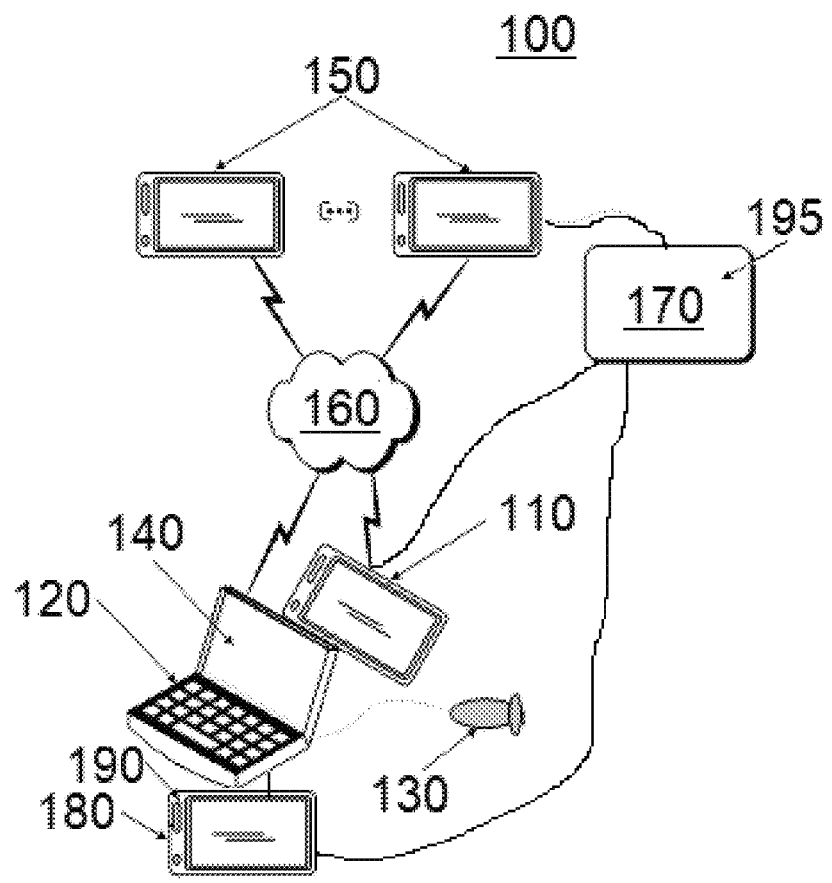
FIG. 1 depicts an example a technical environment into which various aspects of some embodiments of the present invention can be implemented.

The accompanying figures, which are not drawn to scale for ease of understanding, in which like reference numerals may refer to identical or functionally similar elements throughout the separate views and which are incorporated in and form a part of the specification, further illustrate the present invention and, together with the detailed description of the invention, serve to explain the principles of the present invention. As understood by one of skill in the art, the accompanying figures are provided for ease of understanding and illustrate aspects of certain embodiments of the present invention. The invention is not limited to the embodiments depicted in the figures.

Terms

The terms "connect," "connected," "contact" "coupled" and/or the like are broadly defined herein to encompass a variety of divergent arrangements and assembly techniques. These arrangements and techniques include, but are not limited to (1) the direct joining of one component and another component with no intervening components therebetween (e.g., the components are in direct physical contact); and (2) the joining of one component and another component with one or more components therebetween, provided that the one component being "connected to" or "contacting" or "coupled to" the other component is somehow in operative communication (e.g., electrically, fluidly, physically, optically, etc.) with the other component (notwithstanding the presence of one or more additional components therebetween). It is to be understood that some components that are in direct physical contact with one another may or may not be in electrical contact and/or fluid contact with one another. Moreover, two components that are electrically connected, electrically coupled, optically connected, optically coupled, fluidly connected or fluidly coupled may or may not be in direct physical contact, and one or more other components may be positioned therebetween.

The terms "including" and "comprising", as used herein, mean the same thing.

The terms "substantially", "approximately", "about", "relatively," or other such similar terms that may be used throughout this disclosure, including the claims, are used to describe and account for small fluctuations, such as due to variations in processing, from a reference or parameter. Such small fluctuations include a zero fluctuation from the reference or parameter as well. For example, they can refer to less than or equal to ±10%, such as less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%. If used herein, the terms "substantially", "approximately", "about", "relatively," or other such similar terms may also refer to no fluctuations.

As used herein, "electrically coupled" refers to a transfer of electrical energy between any combination of a power source, an electrode, a conductive surface, a droplet, a conductive trace, wire, waveguide, nanostructures, other circuit segment and the like. The terms electrically coupled may be utilized in connection with direct or indirect connections and may pass through various intermediaries, such as a fluid intermediary, an air gap and the like.

As used herein, "neural networks" refer to a biologically inspired programming paradigm which enable a computer to learn from observational data. This learning is referred to as deep learning, which is a set of techniques for learning in neural networks. Neural networks, including modular neural networks, are capable of pattern recognition with speed, accuracy, and efficiency, in situations where data sets are multiple and expansive, including across a distributed network of the technical environment. Modern neural networks are non-linear statistical data modeling tools. They are usually used to model complex relationships between inputs and outputs or to identify patterns in data (i.e., neural networks are non-linear statistical data modeling or decision-making tools). In general, program code utilizing neural networks can model complex relationships between inputs and outputs and identify patterns in data. Because of the speed and efficiency of neural networks, especially when parsing multiple complex data sets, neural networks and deep learning provide solutions to many problems in image recognition, speech recognition, and natural language processing. As described below, the neural networks in embodiments of the present invention provide image recognition capabilities.

As used herein, the term "plenoptic camera" is a light field camera. This light field camera captures information about the light field emanating from a scene (e.g., the intensity of light in a scene, and the precise direction that the light rays are traveling in space). In contrast, conventional cameras only record light intensity.

As used herein, a "mask image" is an image where some of the pixel intensity values are zero, and others are non-zero. Wherever the pixel intensity value is zero in the mask image, the pixel intensity of the resulting masked image can be set to the background value (e.g., zero).

As used herein, the term "clinical display" refers to a display screen of an ultrasound machine.

As used herein, the term "processor" refers to a hardware and/or software device that can execute computer instructions, including, but not limited to, one or more software processors, hardware processors, field programmable gate arrays (FPGAs), application-specific integrated circuits (ASICs), and/or programmable logic devices (PLDs).

As discussed above, various existing ultrasound systems, including those that do provide multiple displays, possess functionality limitations that can impact patient care. The level of care can be improved by utilizing a display system that provides all personnel in an examination room with comparable functionality. As will be discussed herein, embodiments of the present invention provide this functionality.

Embodiments of the present invention include a computer-implemented method, a computer program product, and a computer system where program code executing on one or more processors couples a computing device, such as a tablet, to an ultrasound machine such that the tablet can display useful information during an ultrasound procedure. To this end, the program code generates this useful information, utilizing one or more neural networks. Aspects of the various embodiments of the present invention include, but are not limited to, program code that: 1) communicates ultrasound data, including ultrasound images and other data related to an ultrasound machine, to the computing device; 2) configures resources on the tablet to implement one or more neural networks; and/or 3) jointly operates the computing device and the ultrasound machine. Embodiments of the present invention provide significant improvements over existing systems by enabling enhanced display controls for all users through a more effective implementation of neural networks.

Embodiments of the present invention are inextricably linked to computing at least because the methods, systems, and computer program products described herein include the implementation of neural networks onto various computing devices communicatively coupled to specialized ultrasound computing systems to increase the efficacy of the ultrasound systems as a whole, including the efficiency, functionality, and accuracy of the display(s). FIG. 1, which will be discussed in more detail herein, illustrates a non-limiting example of the technical architecture of an ultrasound system 100 of various embodiments of the present invention. Various computing elements beyond generic computing elements are included in this ultrasound system 100. As discussed earlier, aspects of embodiments of the present invention are directed to the practical application of implementing neural networks on computing devices coupled to ultrasound-specific computing nodes in a manner that increases the efficacy and quality of the imaging and breadth of imaging functionality the program code displays to users of the ultrasound system.

Embodiments of the present invention provide significantly more utility than existing systems at least because they address display challenges of existing systems. Among the challenges are the limited accessibility and functionality of the displays and erroneous labeling from an overly general neural network implementation. First, as discussed above, various challenges exist related to displaying data in existing ultrasound systems, which include a display (e.g., a computing device such as a tablet). While an ultrasound system with a single display is inaccessible to all parties within a medical environment who could contribute to the ultrasound procedure, systems with multiple monitors only service to clone a visual without offering additional medical personnel with the functionality of the operator at the initial display. Second, certain existing systems include a sub-optimal implementation of one or more neural networks. To assist a user during an ultrasound examination, some ultrasound systems generate visual aids for ultrasound images, such as labels (e.g., to distinguish a vein from an artery). These visual aids are useful when program code of an ultrasound system generates the labels and displays them in real-time. To display the labels in real-time, the program code utilizes sophisticated signal processing algorithms, including neural networks, and significant processing resources to implement the algorithms. The technical architectures of the existing systems limit the utility of the functionality because these ultrasound systems implement one or more neural networks in the (off-the-shelf) computing device associated with the display. Although implementing neural networks in computing devices can offload certain processing from the ultrasound-specific hardware and software, because the ultrasound system supports multiple devices from multiple manufacturers, the neural network is architected to operate at processing speeds and with processing resources supported across the multiple devices meaning that the implementation is almost always sub-optimum, in that it does not take full advantage of any specific computing device's resources. Thus, visual aids generated by the ultrasound system may not be acceptable to some users, and in some cases, may interfere with or confuse users. For instance, because the ultrasound system includes a sub-optimum implementation of a neural network, the ultrasound system can misclassify an artery as a vein, resulting in an erroneous needle insertion for a patient. As will be discussed in detail herein, aspects of embodiments of the present invention not only provide greater visibility to all personnel observing an ultrasound procedure performed with an ultrasound system that uses off-the-shelf computing devices with neural networks, but also implement the neural networks in a manner that provides usable imaging for all computing devices of the ultrasound system. Additional advantages of embodiments of the present invention over existing ultrasound systems are noted, in context, below.

FIG. 1 illustrates an example of a technical environment of an ultrasound system 100 into which aspects of some embodiments of the present invention can be implemented. Throughout the description of FIG. 1, the term "computing device" or "computing devices" is used without a designator. When this term is used generally in the context of FIG. 1, the term "computing device" or "computing devices" is being used to refer, collectively to one or more of computing device 110, other computing device 180, and/or additional computing devices 150. These computing devices can include, but are not limited to, personal computing devices, mobile computing devices, tablets, laptops, touchscreen devices, smartphones, etc. The computing devices can be of the same type or of different types. They are numbered separately for ease of understanding when describing the technical environment of FIG. 1.

FIG. 1 will be used herein to illustrate how aspects of embodiments of the present invention: 1) communicate ultrasound data, including ultrasound images or frames and other data related to an ultrasound machine, to a computing device; 2) configure resources on the computing device to implement one or more neural networks; and 3) jointly operate the computing device and the ultrasound machine. The ultrasound system 100 includes a computing device 110, depicted in FIG. 1 as a tablet, which is communicatively coupled and can also be mechanically coupled to an ultrasound machine 120. For instance, the computing device 110 can be fixed to the ultrasound machine 120 using various connectors including but not limited to, screws, bolts, nuts, clamps, etc. The perceived permanence of the mechanical joining is a theft deterrent. The joining of the computing device 110 to the ultrasound machine 120 can also be temporary so that the computing device 110 is convertible, to enable mobile usage of the computing device 110, for example, with a probe 130. In examples where the computing device 110 is convertible, the computing device 110 can be mounted to the ultrasound machine 120 with security devices including, but not limited to smart locks, which can be unlocked via a biometric sensor, such as a fingerprint reader, eye reader, voice recognition system, etc. The ultrasound machine 120 and the computing device 110 are communicatively coupled via a communications network 160 (e.g., wired and/or wireless, bidirectional, etc.) to facilitate communications from the ultrasound machine 120 to the computing device 110 and vice versa.

Both the ultrasound machine 120 and the computing device 110 can display ultrasound data. The ultrasound machine 120 includes a clinical display 140. The computing device 110 can display data that complements the clinical display 140 of the ultrasound machine 120. While the clinical display 140 provides an unencumbered view of ultrasound images, in embodiments of the present invention, program code executing on one or more processing resources of the ultrasound system 100, which can include one or more processors of the computing device 110, can display data and/or overlay data on ultrasound images (e.g., labels of blood vessels, visualizations of interventional instruments, etc.) that is based on inferences made by a neural network running on the computing device 110. The clinical display 140 and the computing device 110 can simultaneously display these different views of the ultrasound data. Conventional ultrasound systems without neural networks are limited to displaying ultrasound images without the visual aids generated by a neural network.

Aspects of embodiments of the present invention communicate ultrasound data, including ultrasound images and other data related to an ultrasound machine, to computing devices, such as the computing device 110. The ultrasound machine 120 communicates with the computing device 110 via a communications network 160. The format of communications between the ultrasound machine 120 and the computing device 110 can vary across various embodiments of the present invention. The program code executing on the ultrasound machine 120 can encode and/or encrypt the ultrasound data before sending these data to the computing device 110. In this example, program code executing on the computing device 110 decodes and/or decrypts the ultrasound data and program code of an ultrasound application 170 executing on the computing device 110 displays the data on the computing device 110. The program code of the ultrasound application 170 displays the data in an interface of the ultrasound application 170. In one example, program code executing on the ultrasound machine 120 encodes ultrasound data (e.g., data regarding an ultrasound examination, including, but not limited to, gain, depth, beam angle, number of transducers used, pulse width, drive level, filter used, etc.), received via an ultrasound probe 130 and/or generated on the ultrasound machine 120, into image data, and communicates these image data to the computing device 110. By encoding these data, the program code of the ultrasound machine 120 can hide (e.g., make imperceptible) these data such that program code of the computing device 110 (e.g., the ultrasound application 170) does not display these data when displaying an ultrasound image. For example, these data can be encoded into image data, and the encoded data can be decoded and removed from the image data prior to displaying an ultrasound image by the computing device 110. In some examples, the ultrasound machine 120 communicates image data to the computing device 110 that includes pre-scan converted image data (e.g., data that has not been rasterized for viewing). Additionally, or alternatively, the program code of the ultrasound machine 120 can transmit image data to the computing device 110 that includes scan-converted image data (e.g., pixel data).

The communications network 160, which provides a communication link between an ultrasound machine 120 and a computing device 110 (e.g., a tablet) in embodiments of the present invention, can support different protocols to facilitate communications between the ultrasound machine 120 and the computing device 110. For example, this communication link can utilize a protocol that supports continuous frames of images, such as high-definition multimedia interface (HDMI). To overcome the limitations of the communication protocol, the program code of the ultrasound machine 120 can utilize encoding schemes to communicate ultrasound data that includes non-image data. For example, the program code of the ultrasound machine 120 can encode the ultrasound data into a representation such as an image of decodable indicia that can be included in an image frame sent using a communication protocol. Images of decodable indicia, which the program code can encode into an image frame can include, but are not limited to, quick response (QR) codes, bar codes (e.g., one-dimensional and two-dimensional bar codes), optical character recognitions (OCRs), glyphs, and/or other visual markings. The computing device 110 can include a decodable indicia reader (e.g., a scanner) to decode the ultrasound data. In this way, the ultrasound machine 120 and the computing device 110 can communicate non-image ultrasound data with a communication protocol designed to support image data (e.g., image frames).

In some examples, the ultrasound machine 120 and the computing device 110 communicate by utilizing a modulator, at the ultrasound machine 120, and a demodulator, at the computing device 110. In these examples, the program code of the ultrasound machine 120 encodes the ultrasound data by generating a carrier signal and modulating a property of the carrier signal according to the ultrasound data. The ultrasound machine 120 transmits the signal wired and/or wirelessly over a communications network 160. The program code of the computing device 110 can implement a demodulator at least partially as a software radio and decode the modulated carrier signal to recover the ultrasound data. The program code of the ultrasound machine 120 can hide the carrier signal within an existing communication link (e.g., the ultrasound machine 120 and the computing device 110 can be coupled via a wireless communication link that occupies a bandwidth). Within this bandwidth, the program code of the ultrasound machine 120 can place the carrier signal in a position where it does not disturb the data in this bandwidth. For example, the carrier signal can comprise a spread spectrum signal, such as by including multiple carrier signals that are frequency hopped, and/or being spread by a spreading sequence.

Program code executing on the computing device 110, in some embodiments, can process signals on the computing device 110 based on features of the computing device 110 and/or knowledge that the data is indicative of an ultrasound examination, or combinations thereof. For instance, program code of the ultrasound system 120 can determine decimation rates and/or bit precisions to fit the processing resources of the computing device 110, knowing that the data is ultrasound data. The program code can decimate in one dimension differently than another dimension, which may be suitable for ultrasound images but unsuitable for generic image data, such as a portrait, family photograph, or landscape scene. As an example, ultrasound data can be oversampled in an axial dimension and under sampled in a lateral dimension. Hence, the ultrasound system can decimate more in the axial direction to reduce the dataset.

In various embodiments, the program code of the ultrasound machine 120 can transmit encoded ultrasound data to the computing device 110 utilizing encoding methods that are camera recognizable and that are not camera recognizable. While a QR code, which was discussed earlier, is a method of encoding that is camera recognizable, the program code of the ultrasound machine 120, in some examples, encodes the ultrasound data in ways that are not detectable by a camera. For example, the program code can encode ultrasound data into a logo that is displayed in an ultrasound image or on a display that displays an ultrasound image. For example, the program code can modulate a given logo to include encoded ultrasound data, including by encoding the ultrasound data into a color scale or grey scale used to represent the logo. For instance, if the pixel data of the logo is represented by eight bits having values 0 . . . 255, with black represented by the value 0, then the black values can instead be represented as 0, 1, or 2, with 1 and 2 values representing a binary modulation. For example, the value of 0 can denote black that is not modulated, the value of 1 can denote black that has been modulated according to a first value (e.g., in a positive direction), and the value of 2 can denote black that has been modulated according to a second value (e.g., in a negative direction). The program code can encode these ultrasound data into these first and second values (or directions) as antipodal signals, and the program code can display the logo so that the modulated data is imperceptible (e.g., by stripping off the modulated data and forcing values of 1 and 2 to zero). The logo can represent a manufacturer of the ultrasound machine 120. Another imperceptible method of encoding that the program code in various embodiments of the present invention utilized is encoding the ultrasound image data in a grey scale represented by N bits. In this example, the program code utilizes only N−M (M<N) bits to represent the ultrasound image. The remaining M bits can be used to encode the hidden ultrasound data. For instance, with N=8 and M=1, the program code utilizes seven bits to represent the ultrasound image and one bit to encode the hidden ultrasound data.

In some examples, the program code of the ultrasound machine 120 makes various determinations about portions of the images and provides these insights to the computing device 110. Similar to the logo example discussed above, in some embodiments, program code of the ultrasound system can determine a region of an ultrasound image that is constant in color and encode the ultrasound data into the constant-hue region using the logo-related modulation techniques described above. The region can be predetermined (e.g., known a priori to the ultrasound machine and tablet) or the program code of the ultrasound machine 120 can determine the region on the fly, and communicate the location of the region to the computing device 110. For instance, the program code of the ultrasound machine 120 can determine a region identifier as modulated pixel numbers, line numbers, position numbers, etc. in header data of the image frames it provides to the computing device 110. The program code of the computing device 110 can read the region identifier from the header to configure a decoder to decode the encoded ultrasound data. This approach has an advantage in the situation when the program code of the ultrasound machine 120 communicates data to the computing device 110 that includes a copy of what is displayed on the clinical display 140 of the ultrasound machine 120 because in this example, the program code of the ultrasound machine 120 can encode the ultrasound data and transmit the ultrasound data to the computing device 110 with little processing burden and throughput overhead.

In an example, the program code of the ultrasound machine 120 can add visual indicators such as lines to images, and the lines can include encoded, hidden ultrasound data. Additionally, or alternatively, the program code of the ultrasound machine 120 can remove a line from an image and replace the removed line with a new line that includes encoded, hidden ultrasound data. The line removed and added can correspond to an edge of an image, making it less perceptible than if the line corresponded to a central portion of the image.

As discussed earlier, a point of utility of embodiments of the present invention is that individuals viewing ultrasound images and data on the display of the computing device 110 and the individual viewing ultrasound images on the clinical display 140, have access to the same data, in real-time, even when the program code of the ultrasound machine 120 transmits these data to the computing device 110. To facilitate this timing, the communication link (via the communications network 160) between the ultrasound machine 120 and the computing device 110 can utilize various technologies and protocols to facilitate the speed of the communications from the ultrasound machine 120 to the computing device 110. For example, the communication link can support data transfer at a frame rate that is greater than the ultrasound frame rate (the rate at which the ultrasound machine 120 generates ultrasound images). In an example, the program code of the ultrasound system marks one or more frames as redundant frames, since the higher transmission frame rate than the ultrasound frame rate means that redundant frames can be communicated by the ultrasound machine 120 to the computing device 110 together with ultrasound images, without loss of information of the ultrasound images. The program code of the ultrasound machine 120 can encode ultrasound data into the redundant frames, such as with a bar code, QR code, etc.

By communicating redundant frames that include coded ultrasound data, program code in embodiments of the present invention can facilitate real-time displays of ultrasound data in both the clinical display 140 and in the display of the computing device 110. The program code of the computing device 110 can determine which frames received from the ultrasound machine 120 are redundant frames by reading the mark inserted by the program code of the ultrasound machine 120. This program code of the ultrasound machine 120 can insert this mark in file locations including but not limited to, a header or metadata of the frames. When the program code of the computing device 110 identifies one of the redundant frames, rather than displaying the redundant frame as ultrasound image data and/or processing the image data with a neural network, the program code of the computing device 110 can pass the redundant frame to a decoder module of the ultrasound application 170. The program code of the decoder module can determine the type of code applied to the redundant frame and decode the ultrasound data from the redundant frame using a decoder (e.g., a QR decoder). In some examples, the program code of the computing device 110 displays the decoded data in an interface of the computing device 110 (e.g., in a sidebar of a user interface that displays parameters of the ultrasound examination communicated via the encoded ultrasound data, such as a gain, angle, system or probe identification number, operator identification number, preset value, and the like). In this example, the program code of the computing device 110 displays information that may or may not be displayed on the clinical display 140 of the ultrasound machine 120.

In some examples, accuracy of the ultrasound system is increased when the program code of the ultrasound machine 120 transmits pre-scan converted ultrasound data to one or more computing devices, via the communications network 160, instead of scan-converted data that has been rasterized for display. Pre-scan converted data accounts for geometry/propagation direction when applying different decimations to different dimensions, as described herein. The computational burden to undo scan conversion after the fact would be very high, which would increase the value of having the neural network get data before it is ready for the screen. In some embodiments of the present invention, the simplest way to get image data to the tablet is for the ultrasound machine 120 to transmit the final, scan-converted image. Linear format scanheads are simpler in this regard, while phased and curved arrays would benefit more.

Aspects of some embodiments of the present invention can configure resources on a computing device (e.g., a tablet) to implement one or more neural networks. In addition to being in varied formats, the program code of the ultrasound machine 120 can communicate ultrasound data to the computing device 110 that includes different types of information. In some examples, the ultrasound data can include configuration parameters to configure and/or control the computing device 110, including configuration parameters to configure a user interface on the computing device 110, etc. A neural network implemented on the computing device can utilize these parameters (e.g., architecture definitions, numbers of layers, weight selections, filter lengths, a selection of one neural network from multiple neural networks available, etc.). The configuration parameters can also include user permissions or authentication protocols that enable or disable an operator of the tablet from communicating with and/or controlling the ultrasound machine 120. In one example, the program code of the ultrasound machine 120 encodes ultrasound data into redundant frames and includes in these redundant frames, configuration parameters related to the ultrasound examination, for controlling/configuring the computing device 110.

Aspects of some embodiments of the present invention jointly operate the computing device and the ultrasound machine. While the program code of the ultrasound machine 120 communicates with the computing device 110 over the communications network 160, the program code of the computing device 110 can also communicate with the ultrasound machine 120 over the communications network 160. The program code of the computing device 110 can send various data to the ultrasound machine 120 including information (e.g., messages, configuration parameters, etc.) as well as images. Regarding the information example, the program code of the ultrasound machine 120 can obtain this information and display the information on the clinical display 140 of the ultrasound machine 120, or on an additional display of the ultrasound machine 120, including but not limited to another computing device 180 that is fixed/anchored to the ultrasound machine 120. This functionality can be utilized by an operator of the computing device 110 (e.g., a nurse) who is collocated with an operator of the ultrasound machine 120, or a specialist remote from the ultrasound machine 120. The operator of the computing device 110 can send a comment, from the computing device 110, to the ultrasound machine 120. Program code of the ultrasound machine 120 obtains the comments and displays the comment on the clinical display 140 (see, e.g., FIG. 2, 204) or on the other computing device 180. In an example, the ultrasound machine 120 displays a section, such as a sidebar, configured to display comments and information sent from the computing device 110 and/or additional computing device 150, which are communicatively coupled to the ultrasound machine 120, via a communications network 160.

The communications between various entities in FIG. 1 are described in a manner to allow an individual to trace specific scenarios and not to imply any exclusivity. Given that the entities of the technical environment of FIG. 1 are interconnected, each computing device 110, 150, and 180 can communicate directly and/or indirectly with the other entities within the technical environment. The example discussed below is provided as an example of communications that describe certain functionalities of the various examples disclosed herein. Regarding the image example, in some examples, the program code of the computing device 110 communicates an image to the ultrasound machine 120. The program code of the ultrasound machine 120 obtains and displays the image (e.g., on the clinical display 140 or on a display of the computing device 180). During an ultrasound examination, an operator of a computing device 110 may rewind, zoom, or edit an ultrasound image to form a tablet-generated image. The operator of the computing device 110 may send, via the communication network 160, the tablet-generated image to the ultrasound machine 120.

The ultrasound machine 120 obtains and displays the tablet-generated image. In one example, the tablet-generated image includes an image from a different perspective than a current perspective of an image displayed live on the clinical display, such as an image corresponding to an earlier portion of the ultrasound exam.

The ultrasound system 100 of FIG. 1 also includes one or more additional computing devices 150 (e.g., tablets), which are communicatively coupled to the ultrasound machine 120. In this example, the additional computing devices 150 communicate with the ultrasound machine 120 via communication link 160, e.g., a two-way wireless link. In a medical setting, the wireless connectivity of the additional computing devices 150 to the ultrasound machine 120 enables individuals in a medical facility to position the additional computing devices 150 at locations proximate to as well as remote from where a patient is being treated. Additional computing devices 150 located in or near the examination room can be operated by doctors, nurses, sonographers, and/or other trained clinicians. Meanwhile, additional computing devices 150 at remote locations can enable collaboration between medical providers as an ultrasound examination (e.g., a knee examination) may be performed by a sonographer in a first city, and one of additional computing devices 150 may be operated by a specialist (e.g., orthopedist who specialized in knees) in a second city. In one example, a patient operates the ultrasound machine 120 and an ultrasound operator operates the additional computing devices 150, enabling the patient to be remote from the clinician in a telemedicine setting.

Additionally or alternatively to the computing device 110, in some examples, one or more of the additional computing devices 150 can execute neural networks as well as an ultrasound application 170. Accordingly, the examples herein provide advantages over existing ultrasound systems by enabling collaboration through inputs from additional users (e.g., trained clinicians). During an ultrasound examination, the additional computing devices 150 can receive ultrasound images from the ultrasound machine, execute a neural network on the additional computing devices 150 to process the ultrasound images, and display on the additional computing devices 150 visual aids (e.g., labels, assistive representations, etc.). Because the ultrasound machine 120, the computing device 110, the other computing device 180, and the additional computing devices 150 can communicate with each other via the network 160, individuals utilizing the ultrasound machine 120, the computing device 110, the other computing device 180, and the additional computing devices 150 can collaborate with each other. For example, users of the computing device 110, and the additional computing devices 150 can communicate, in real time, over the two-way communication link in the communications network 160 during the ultrasound examination, to the operator of the ultrasound machine 120, and the comments communicated from the computing device 110, and the additional computing devices 150 can display on the clinical display 140, including on a sidebar (which was discussed earlier) (see, e.g., FIG. 2, 204). The users of the additional computing devices 150 (e.g., trained professionals) can perform operations on the images displayed on the additional computing devices 150 (e.g., freezing the ultrasound images, rewinding, zooming, and/or enabling one or more neural networks to generate and display user-selected visual aids, etc.), which give rise to the insights that the users provide, electronically, to other parties. In some examples, a user of one of the additional computing devices 150 can utilize the device to remotely configure the ultrasound machine 120 (e.g., by setting a gain, beam angle, pulse width, etc.) to generate ultrasound images.

The collaborative advantages of some embodiments of the present invention are realized in training-related settings. In an educational setting, operators of the additional computing devices 150 and/or the computing device 110 may be students, and an operator of the ultrasound machine 120 may be a trained professional or instructor. The students may be remote from the instructor. The ultrasound application 170 enables the students to communicate via the network 160 among themselves or with the instructor. Hence, the students can participate in an online course or training session in real-time. Expanding on this example, the program code of the ultrasound application 170 (e.g., executed on a processor system 195) can determine metrics from the additional computing devices 150 and/or the computing device 110 and communicate these metrics to the instructor to improve the usefulness of the online session. The program code can determine, for example, that students have rewound the ultrasound images to a particular portion of the online session, such as during a needle insertion performed by the instructor. The program code can communicate the number of students and an indicator of the particular portion to the instructor, so that the instructor may then repeat this particular portion of the ultrasound examination.

As discussed above, in some examples, the computing device 110 and one or more of the additional computing devices 150 can utilize various neural network, machine learning, artificial intelligence (AI), adaptive system, etc. (generally referred to as AI or a neural network) to assist in ultrasound examinations. In embodiments of the present invention, program code comprising the neural networks recognize and distinguish various objects in ultrasound images. To this end, image recognition capabilities can be implemented as a machine learning system that includes a neural network. In certain embodiments of the present invention the program code utilizes supervised, semi-supervised, or unsupervised deep learning through a single- or multi-layer neural network to identify objects in images from the ultrasound machine 120, which receives and processes data from the probe 130. The program code can utilize resources of the neural networks to train machine learning algorithms to identify objects, to identify connections between objects, and to weight the importance of the objects (e.g., to rank and/or quantify the identified objects based on urgency). Training data includes ultrasound images of the objects to train the machine learning algorithms and to generate a classifier or model to classify entities. The program code of the neural networks can continue to train and re-train the algorithms, which can update the classifier, over time, based on the images obtained from the ultrasound machine 120. Thus, the neural networks can identify certain key features of objects in the images from the ultrasound machine 120. Hence, by utilizing neural networks, the program code can identify objects, classify these objects based on importance, and/or provide a recommendation. The program code can determine the importance of objects based on comparing the objects to training data provided to the system that includes historical images with regions of interest identified and importance levels assigned to these regions.

Embodiments of the present invention can include neural networks that generate inferences specific to certain ultrasound image features. In one example, the computing device 110 and, optionally, one or more of the additional computing devices 150, include a neural network that receives ultrasound images and generates inferences for blood vessels in the ultrasound images. The inferences can include a classifier of whether the blood vessel is a vein or artery, a confidence level of the classification, a property of the blood vessel, such as a diameter, major and minor ellipse sizes, a level of pressure or compaction of the blood vessel, etc. Additionally, or alternatively, the inferences can include a recommendation about the ultrasound examination related to the blood vessel, such as a recommended catheter size, a recommended insertion point of an interventional instrument, a recommended insertion angle for an interventional instrument, a recommended depth, and the like. Additionally, or alternatively, the computing device 110 and, optionally, one or more of the additional computing devices 150 include a neural network that receives ultrasound images and generates inferences for cardiac properties based on the ultrasound images. For instance, the neural network can generate parameters for cardiac functions, such as ventricle volumes and ejection fraction. In an example, the neural network generates segmentations of anatomical features, such as segmentations of a heart ventricle, a bladder, a blood vessel, etc.

In various examples, specific neural networks and classifiers are implemented on some of the additional computing devices 150, as opposed to on the ultrasound machine 120. One reason for implementing the specific neural networks on one or more of the additional computing devices 150 is because some ultrasound machines may include legacy software and/or hardware with less flexibility for implementing neural networks. Just as an ultrasound machine 120 may not include sufficient processing capabilities to execute a neural network, a given additional computing device 150 may not include sufficient processing capabilities to execute a neural network. Because the various computing devices are networked, this additional computing device 150 can utilize a neural network on a different computing device to gain image insights. For example, program code comprising the ultrasound application 170 can determine that the given additional computing device 150 comprises insufficient resources to implement a neural network. The program code of the ultrasound application 170 can then query another one of the additional computing devices 150 to locate a device with the resources to implement the neural network. This device can provide data derived from the neural network to an initial device (e.g., the ultrasound machine 120) during an ultrasound examination.

By utilizing neural networks implemented on one or more computing devices, the program code of the computing device can generate inferences and communicate these inferences, including data related to the inferences, to the ultrasound machine 120. Upon receiving the inferences, the program code of the ultrasound machine 120 can display visual aids based on the inferences. For example, the program code of the one or more computing devices can communicate visual designations including, but not limited to, labels, positions of labels, properties of labels (e.g., colors), to the ultrasound machine 120. The program code of the ultrasound machine 120 can obtain this label information and apply the labels to the clinical display 140.

In an example, the program code of the one or more computing devices generates a mask image. The program code can generate the mask image based on inferences made by a neural network on the computing device. The mask image may include color-coded bounding containers of blood vessels, a representation of an interventional instrument, a segmentation of a body part, a region of interest, combinations thereof, and the like. The program code of the computing device transmits the mask image, via the network 160, to the ultrasound machine 120. The program code of the ultrasound machine 120 can generate a composite image from the mask image and an ultrasound image, including but not limited to, blending pixels from the two images, and/or superimposing the mask image on the ultrasound image. In some examples, the program code of the ultrasound machine 120 displays the composite image on the clinical display 140.

In some embodiments of the present invention, a neural network does not generate an inference for every image frame the ultrasound machine 120 provides to the computing device, via a communications network 160. The neural network can sometimes handle a fixed amount of the analyses due to hardware and/or software shortcomings. For example, if the ultrasound machine 120 provides data to a computing device at a frame rate that is greater than the determined frame rate for the neural network, program code of the ultrasound application 170 executing on the computing device can provide some of the image data to the neural network so that the neural network can generate inferences for the images input to the neural network. For skipped image data not provided to the neural network, the program code of the ultrasound application 170 can include an optical flow algorithm to track the inferences of the skipped frames, (i.e., the frames not processed by the neural network). For example, frames f1, f2, f3, . . . represent image frames provided from the ultrasound machine to the tablet. The program code of the ultrasound application determines a maximum frame rate for a neural network based on the frame rate of the ultrasound data and available resources of the computing device and selects ones of the image frames to be provided to the neural network. If the ultrasound application determines the maximum frame rate for the neural network as ⅓ of the ultrasound frame rate, then the program code of ultrasound application provides every third frame of data to the neural network, e.g., f1, f4, f7, etc., and the skipped frames e.g., f2, f3, f5, f6, etc., to the optical flow algorithm, which can track the inferences made by the neural network over the skipped frames.

Rather than process a set percentage of frames, the neural network can generate inferences from frames identified by the program code. In some examples, program code of the ultrasound system 120 determines which ultrasound frames to process with the neural network on the computing device based on one or more physiological properties of the subject being examined with the ultrasound system. For instance, the ultrasound system can include a cardiac sensor (e.g., EKG terminals) that detects a cardiac signal for a patient. The ultrasound system can synchronize the frames of the ultrasound data processed by the neural network with a cardiac signal of the patient, including by providing the ultrasound frames that correspond to a systole phase of the cardiac signal to the neural network for inference generation, and using the optical flow algorithm on the ultrasound frames that correspond to a diastole phase of the cardiac signal. The physiological signal can include any suitable signal from any suitable sensor, such as respiratory signals, cardiac signals, nervous system signals, optical signals (e.g., derived from an eye feature), image signals (e.g., signals derived from image data) that indicate a relative position of a body part, such as a bone or nerve, and the like, and synchronize the processing of the neural network to generate inferences with one or more features of the physiological signal.

Of the elements that comprise the ultrasound system 100, arguably, the most flexible are the computing devices, which include the computing device 110, the other computing device 180, and the additional computing devices 150. The ultrasound machine 120 itself is sometimes a legacy system with limited software or hardware flexibility. Thus, various functionalities can be provided by the computing devices which may not be available in the ultrasound machine 120. In some examples, a computing device can include a light field processor. For instance, the processor system 195 can include a light field processor that estimates the light field of an image by simulating a plenoptic camera. As illustrated in FIG. 1, in some examples, the processor system 195 is part of the ultrasound application 170 executing on the one or more computing devices 150. The processor system 195 can include one or more neural networks trained to generate a light field from multiple images. Utilizing the functionality provided by the processor system 195, an operator of a computing device can manipulate the light field via the ultrasound application 170 to change the perspective of the image, generate a manipulated image, and transmit this manipulated image to the ultrasound machine 120, via the communications network 160. By manipulating the image, the user of the computing device recommends to the operator of the ultrasound machine 120 to change ultrasound settings, including but not limited to, beam angle and/or probe orientation. Additionally, or alternatively, the ultrasound machine 120 can include a light field processor (not pictured) that estimates the light field of an image so that the ultrasound machine 120, itself, can change a perspective of the image based on the light field.

The computing devices in the ultrasound system 100 can control the functionality of the ultrasound machine 120. Actions taken by a user at a computing device can change an image displayed on the clinical display 140 of the ultrasound machine 120 and can also set parameters of the ultrasound machine 120 to improve the ultrasound procedure itself. Regarding image changes, when a user utilizes a computing device to edit an image, the program code of this computing device can transmit the edits to the ultrasound machine 120. The program code of the ultrasound machine 120 can implement the edits. A specific example of a user edit that can be communicated from a computing device to the ultrasound machine 120, where the ultrasound machine implements the edit, is zooming. Program code transmits and implements zoom levels from the computing device to the ultrasound machine 120 clinical display 140. The ultrasound machine 120 can include a user-selectable control to allow or disallow automatic image editing based on edits made on the computing device.

Regarding the functionality changes, in some examples, program code of a computing device can send information to the ultrasound machine 120 which the ultrasound machine 120 utilizes to adjust its parameters to improve operation (e.g., imaging quality). As an example, an operator of a computing device selects a region of interest in a displayed image. Program code from the computing device communicates the region of interest to the ultrasound machine 120, via the communications network 160. Based on obtaining the region of interest, the program code of the ultrasound machine 120 sets ultrasound parameters (e.g., gain, depth, angle, and/or spatial compounding) to better image the region of interest. The program code of the ultrasound machine 120 and the computing device can display images subsequently obtained by the probe 130, based on these parameters.

In some examples, program code from the computing device configures a neural network based on a region of interest, such as a user-selected region of interest. Program code executed by a processing resource of a computing device can set neural network parameters (e.g., filter weights and lengths, skip connections, patch size, etc.) based on the user-selected region of interest, based on options including but not limited to, size, depth, and/or content of a region of interest. Additionally or alternatively, a user can set neural network parameters through a user interface of a computing device.

In one example, program code executing on a computing device selects a neural network from among a plurality of neural networks available on the computing device, based on the region of interest. For instance, the program code can determine that the region of interest includes a cardiac component and select a neural network trained with images of hearts, rather than a neural network trained with images of lungs. The program code of the ultrasound machine 120 can set ultrasound configuration parameters (e.g., spatial compounding parameters) for a region of interest obtained from a computing device. The program code of a computing node (e.g., a computing device) can configure the neural network based on this region of interest.

Figure 2:
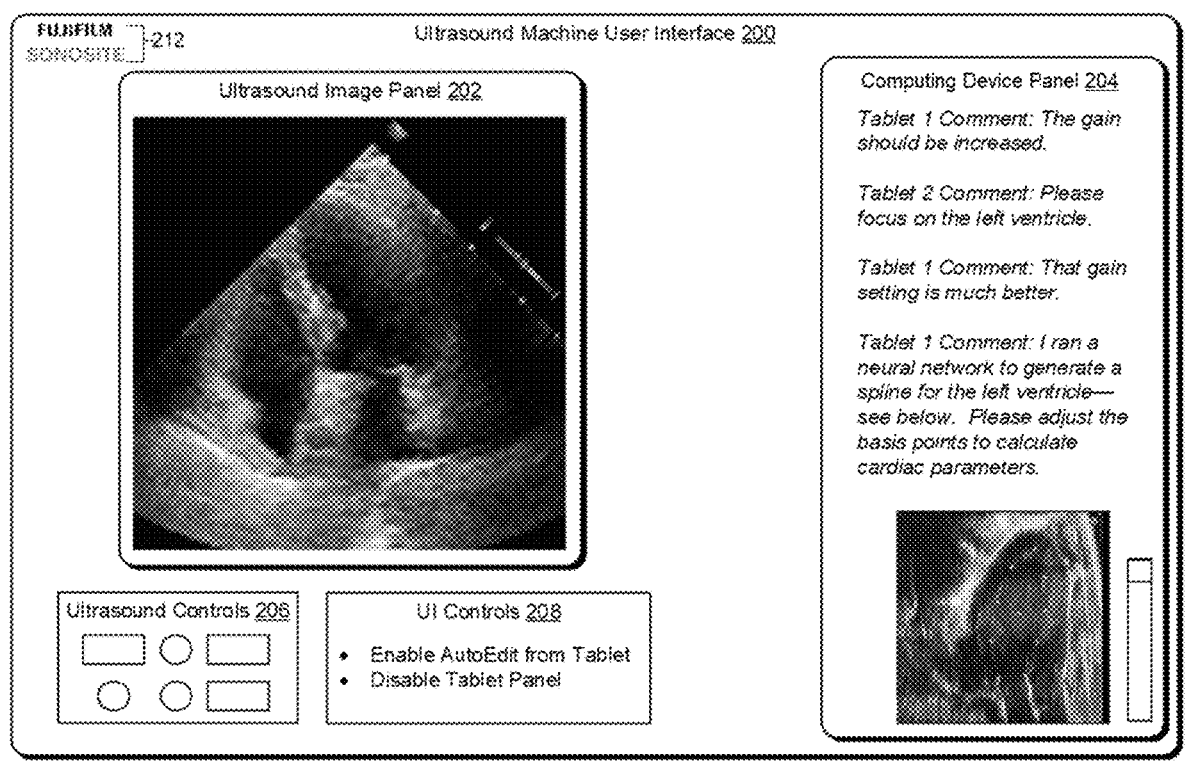
FIG. 2 depicts an example of a visual interface generated in various aspects of the present invention.
Figure 3:
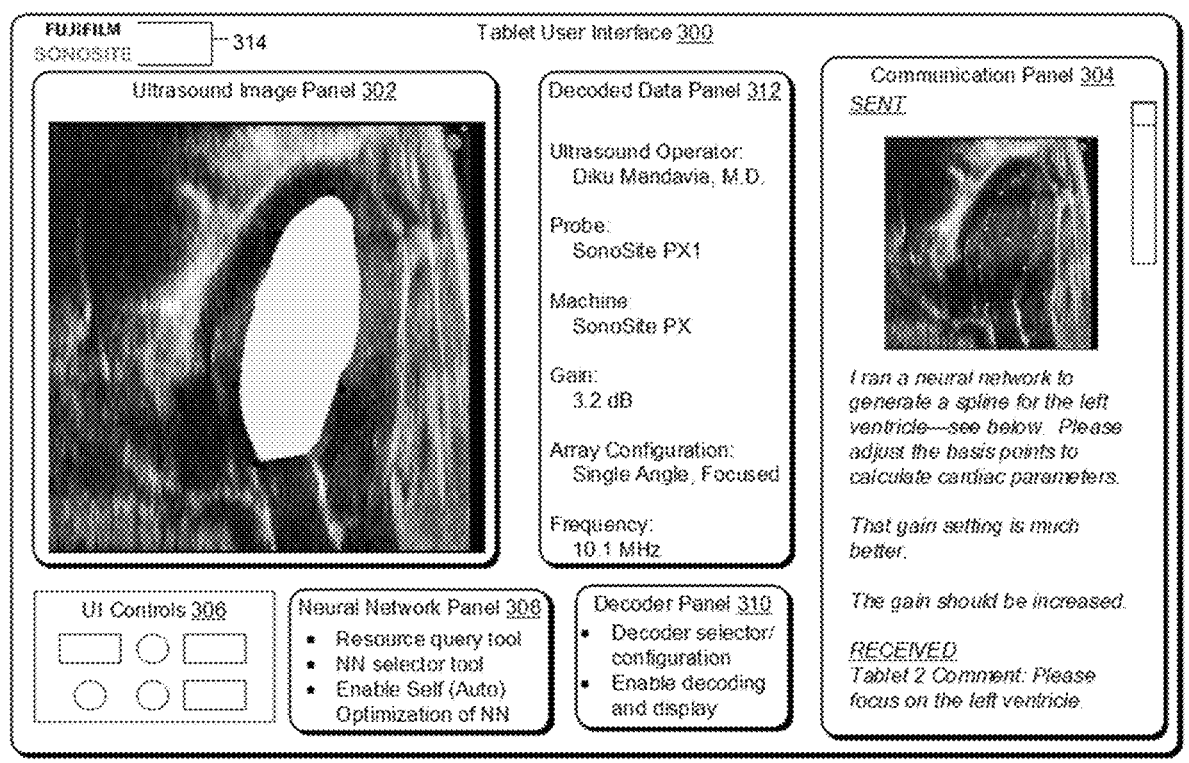
FIG. 3 depicts an example of a visual interface generated in various aspects of the present invention.

As discussed above, the user interfaces of the ultrasound machine 120 and of the computing devices can differ to provide the users of these devices in the ultrasound system 100 with different functionality. Also, elements of the interfaces can display communications between the devices. FIG. 2 includes an example of a user interface 200 of an ultrasound machine (e.g., FIG. 1, 120) while FIG. 3 includes an example of a user interface 300 of a computing device (e.g., FIG. 1, computing device 110, other computing device 180, and/or additional computing devices 150), like a tablet, communicatively coupled to the ultrasound machine (e.g., FIG. 1, 120). In one example, a difference between the ultrasound machine (e.g., FIG. 1, 120) and the computing devices (e.g., FIG. 1, computing device 110, other computing device 180, and/or additional computing devices 150) can include that neural networks can be implemented on or accessible to the computing devices (e.g., FIG. 1, computing device 110, other computing device 180, and/or additional computing devices 150). Thus, inferences and classifications from one or more of the neural networks can be displayed in the user interface 300 of the computing devices (e.g., FIG. 1, computing device 110, other computing device 180, and/or additional computing devices 150). The user interfaces 200, 300 of FIGS. 2 and 3 illustrate how embodiments of the present invention can jointly operate the computing device and the ultrasound machine.

The user interface 200 of the ultrasound machine (e.g., FIG. 1, 120), also referred to as a clinical display, (e.g., FIG. 1, 140) includes an ultrasound image panel 202 that displays an ultrasound image. The ultrasound image panel 202 can also display ultrasound data, including but not limited to, probe settings, etc. The user interface 200 also includes computing device (e.g., tablet) panel 204, which can display information received from a tablet, and information sent to a tablet. In the example, the computing device panel 204 includes comments from computing devices labeled tablet 1 and tablet 2, and an image sent from tablet 1. The image from tablet 1 includes an inference from a neural network implemented in the tablet 1 (in the example, a spline for a left ventricle of a heart). Tablets 1 and 2 are examples of computing devices 150, other computing device 180, and computing device 110 in FIG. 1. The user interface 200 in this example displays a logo 212. In embodiments of the present invention, the program code can modify or modulate this logo 212 to carry ultrasound data in a hidden way, including modulating the logo to include encoded ultrasound data, as discussed herein.

The user interface 200 also includes user controls 206 for controlling the ultrasound machine, such as controls for gain, depth, presets, drive signals, filters, pulse widths, etc. The user interface 200 also includes user interface (UI) controls 208, which includes controls for the user interface 200, including but not limited to, controls for communicating with, and displaying data from, the computing devices (e.g., the collective computing devices of FIG. 1). For example, the UI controls 208 can include a control to enable an automatic edit function from a tablet. When a remote user interacts with the user interface of the computing devices, the changes implemented on the computing device can be implemented in the user interface 200. Hence, this remote user may be able to configure the ultrasound machine. The UI controls 208 can also include a control, e.g., a tablet panel control, to enable and disable functionality available on the computing devices. For instance, when the tablet panel control is disabled, the tablet panel 204 can be minimized, the ultrasound image panel 202 can be maximized, etc. When the tablet panel control is enabled, the tablet panel 204 can be displayed in the user interface 200.

The user interface 300 of the computing device (e.g., FIG. 1, computing device 110, other computing device 180, and/or additional computing devices 150) includes an ultrasound image panel 302 that displays an ultrasound image, such as a composite image that includes content from an image displayed on the ultrasound image panel 204 of the user interface 200 and information based on an inference made by a neural network implemented on a computing device (e.g., a tablet). In this example, the ultrasound image panel 302 displays a segmentation of the left ventricle overlaid on the ultrasound image.

The user interface 300 also includes communication panel 304, which can display information sent from the computing device, and information received on the computing device, including from the ultrasound machine. In the example in FIG. 3, the communication panel 304 displays an ultrasound image with a spline overlaid on the left ventricle that was sent to the ultrasound machine, and a message received from tablet 1. The user interface 300 also includes UI controls 306, which can include any suitable control for configuring and operating the user interface 300, such as controls for zoom, freeze, rewind, etc.

Unlike the user interface 200 of the ultrasound machine, the user interface 300 also includes a neural network panel 308, which includes controls for selecting and configuring neural networks on the computing device. For instance, the neural network panel 308 can include a resource query tool that, when enabled, analyzes the computing device's resources (e.g., native AI instruction set, API sets, memory, speed, processor types, etc.), and can configure a neural network based on the results. This process of configuring a neural network is discussed in more detail with regards to FIG. 4. The neural network panel 308 also includes a neural network selector tool, which can allow a user to select and enable a neural network from among a plurality of available neural networks. For instance, a user may select a first neural network suitable for inferences on ultrasound images of hearts, and a second neural network suitable for inferences on ultrasound images of blood vessels, based on the type of ultrasound examination being performed. The neural network panel 308 also includes a control to enable/disable an automatic, or self-optimization mode of the neural network. When enabled, this mode can configure a neural network to analyze ultrasound images (e.g., generating inferences from the images), and based on the results, reconfigure the neural network to make better inferences, as described above.

The user interface 300 also includes decoder panel 310 that includes controls to configure and select decoders used to decode ultrasound data that can be hidden in the image frames sent from the ultrasound machine to the tablet. The decoder panel 310 can include a control to enable/disable decoding of the ultrasound data, and its subsequent display, as well as controls to select and configure a specific decoder. For instance, a QR decoder can be selected to decode QR images in redundant frames sent from the ultrasound machine. Additionally, or alternatively, a logo decoder can be enabled to decode ultrasound data that can be embedded in a logo, as described above (e.g., FIG. 2, 212). The user interface 300 also includes the decoded data panel 312 that displays the ultrasound data that is decoded. In examples herein, the program code can utilize logos to carry ultrasound data. In some examples, the program code of the ultrasound machines sends a data-bearing logo. Program code in embodiments of the present invention strips the data from the logo and displays the decoded data in the decoded data panel 312. Thus, the logo 314 in FIG. 3 is an example of a logo without the data, as the program code stripped the data and displayed the data in the decoded data panel 312.

Figure 4:
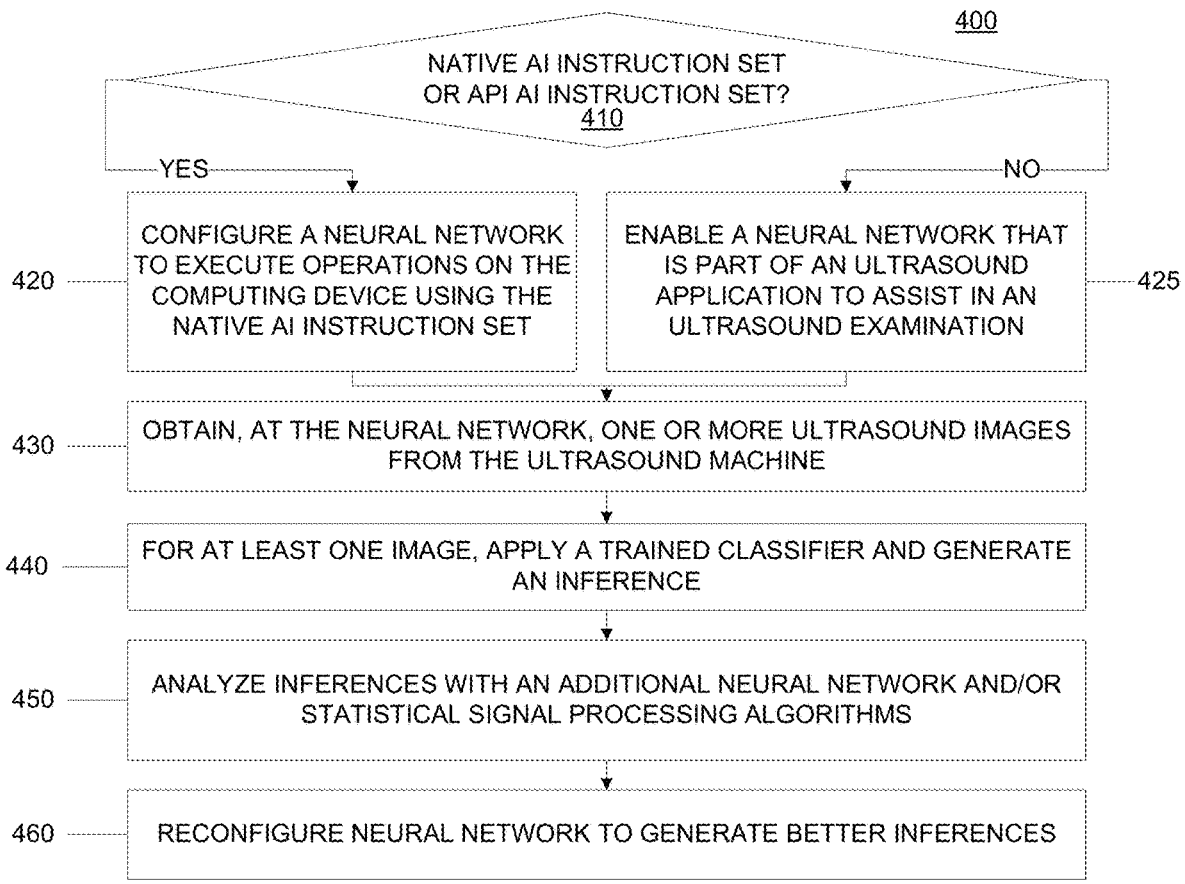
FIG. 4 depicts an example of a workflow for implementing a neural network in some embodiments of the present invention.
Figure 5:
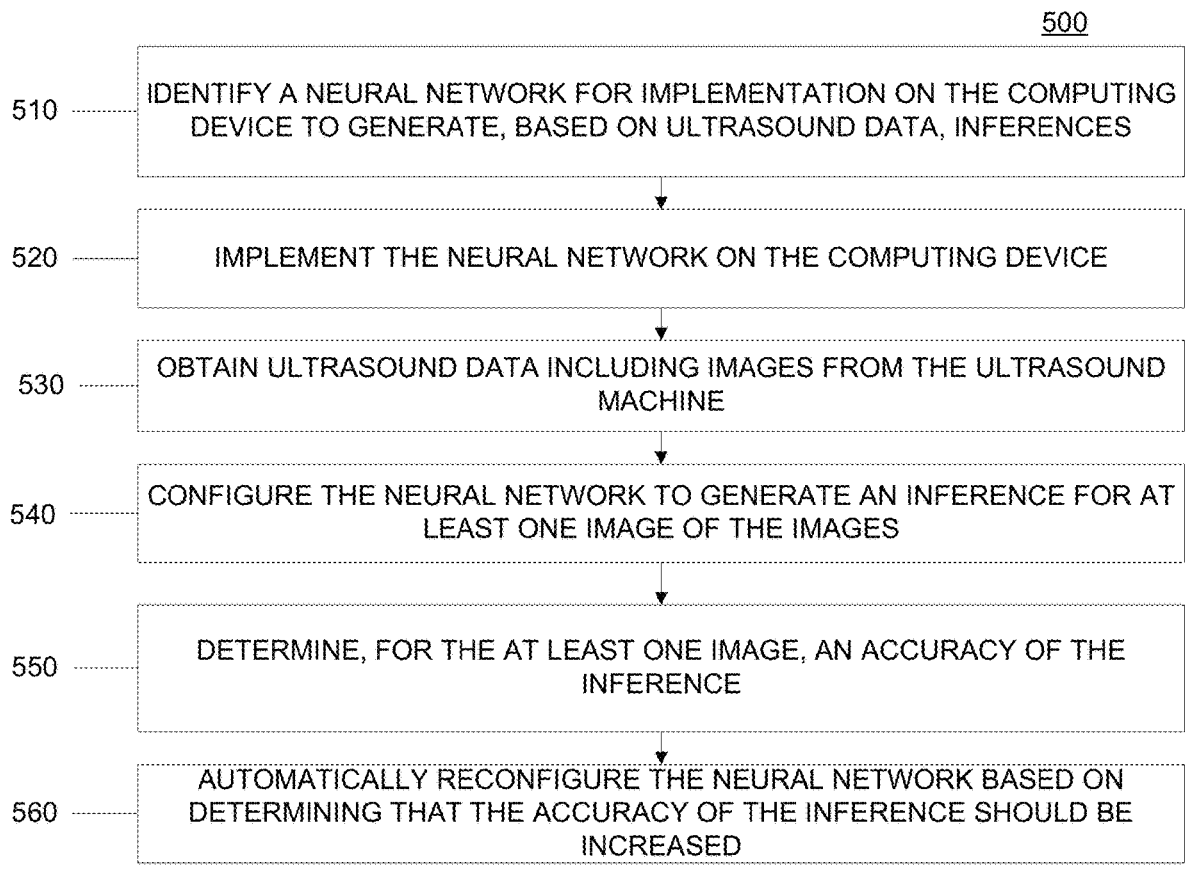
FIG. 5 depicts an example of a workflow for implementing a neural network in some embodiments of the present invention.

FIG. 4 and FIG. 5 illustrate examples of workflows 400, 500 for configuring a computing device communicatively coupled to an ultrasound machine to implement one or more neural networks. The processes comprising these workflows 400, 500 can be performed by processing logic that can include hardware (e.g., circuitry, dedicated logic, memory, etc.), software (such as is run on a general-purpose computer system or a dedicated machine), firmware (e.g., software programmed into a read-only memory), or combinations thereof. In some embodiments, the process is performed by one or more processors of a computing device in an ultrasound system, such as, for example, but not limited to, an ultrasound machine with an ultrasound imaging subsystem, a computing device coupled to an ultrasound machine, such as a tablet, or combinations thereof.

In some embodiments of the present invention, program code executing in the ultrasound system 100 manages various resources of the ultrasound system 100. FIG. 4 illustrates a workflow 400 that depicts the ultrasound system managing resources based on a computing device (e.g., tablet) coupled to an ultrasound machine, such as the computing device 110 coupled to the ultrasound machine 120 in FIG. 1. FIG. 4 illustrates an example of a workflow 400 where program code executing on one or more resources of an ultrasound system determines an architecture of a neural network. The program code determines the architecture based on the computing device utilized to display ultrasound images (e.g., FIG. 1, 110) by configuring resources for the neural network based on aspects including but not limited to, amount, type, availability, and/or combinations thereof of resources of the computing device.

Referring to FIG. 4, program code executing on a resource of an ultrasound system determines if a computing device (e.g., FIG. 1, 110) includes neural network resources that can be used to assist an ultrasound examination. For instance, the program code of the ultrasound system determines whether the computing device includes a native AI instruction set or whether an application programming interface (API) AI instruction set to configure a neural network (410). To determine whether the computing device includes a native AI instruction, the program code can query a configuration file, operating system, device ID, and/or resource manager of the computing device. Additionally, or alternatively, to determine whether the computing device includes a native AI instruction set, the program code can determine whether the computing device includes and/or supports different application programming interfaces (APIs) for configuring neural networks (e.g., loading parameters, connecting layers, etc.) on the computing device.

In some examples, the program code identifies that an appropriate AI instruction set is accessible, such as an API AI instruction set. A given computing device can have more than one application installed with neural networks, built directly into the applications that are accessible via an API, optimized for execution on the specific computing device resources. Additionally, or alternatively, the given computing device can include different versions of the same neural network that are optimized/configured to run on different processors or with different resources of the computing device (e.g., a graphics processing unit (GPU), computer processing unit (CPU), digital signal processor (DSP), or a dedicated AI computer resource (e.g., an ASIC or FPGA)). Some ultrasound systems include a central repository of variations of the neural networks, e.g., the central repository can be included in the ultrasound machine (FIG. 1, 120). In this architecture, the program code can determine whether the computing device includes a native AI instruction set by querying the computing device about its hardware and API capabilities. Based on the responses from the computing device to the query, the program code of the ultrasound machine can identify from the central repository (and transmit) an appropriate neural network model to run on the computing device.

Based on determining that the computing device includes a native AI instruction set or identifying an appropriate instruction set (e.g., an API instruction set), the program code configures a neural network to execute operations on the computing device using the identified AI instruction set (e.g., native AI instruction set or appropriate AI instruction set) (420). To configure the neural network, the program code can connect layers of the network, define skip connections for the network layers, set coefficients (e.g., convolutional coefficients) to trained values, set a filter length, and determine a patch size (e.g., a n×n pixel area of the image, where n can be 3, 4, etc.). In some examples, an API on a given computing device can configure the neural network, including loading the parameters and connecting the layers. For instance, an Open VINO (Intel Inc) optimized network could run on a CPU with OpenVINO libraries (API), and a TensorFlow (Google Inc) Lite network could run on an Android OS-based device with TensorFlow Lite runtime libraries (API).

In some examples, the program code determines that the computing device does not include a native AI instruction and no AI instruction set is available for use on a system resource (410). For example, the program code can determine that a given computing device does not include a native AI instruction set or an API set to configure a neural network. Based on this determination, the program code of an ultrasound application installed on the computing device enables a neural network that is part of the ultrasound application to assist in an ultrasound examination (425). In one example, the ultrasound application includes multiple neural networks and the program code selects one of the multiple neural networks to enable based on one or more features of the computing device (e.g., a display size). As part of enabling the neural network, in some examples, the program code configures the neural network based on one or more features of the computing device (e.g., display size, processor speed, amount of memory, etc.).

Because the computing devices (e.g., FIG. 1, 110, 150, 180) can vary across a technical architecture (e.g., FIG. 1, 100) of an ultrasound system, program code of an ultrasound application can implement different neural network configurations on different devices. Program code of the ultrasound application can configure a neural network in a first configuration for implementation on a first computing device, and a second configuration for implementation on a second computing device. If the program code of the ultrasound application determines that the second computing device has more available resources than the first computing device, then the program code of the ultrasound application can set the second configuration to include more or longer filters in the neural network compared to the first configuration. The neural network configured by the ultrasound application can be used to generate visual data that is included in ultrasound images, such as labels for blood vessels and representations of interventional instruments, as described above. A computing device can display a composite image that includes features of an ultrasound image provided to the computing device from the ultrasound machine and features of an inference made from the neural network, e.g., a label, recommendation, or visual representation of an interventional instrument, such as a needle.

Thus, as illustrated in the workflow 400 of FIG. 4, in embodiments of the present invention, program code of an ultrasound system enables a neural network on a computing device utilizing one or more of: 1) a native AI instruction set; 2) an API; and 3) an ultrasound application executing on the computing device. The program code can customize the implementation based on characteristics of the computing device, including but not limited to, processor speed, memory size, etc. Additionally or alternatively to customizing the neural network to the computing device, the program code can identify characteristics of the ultrasound machine in configuring the neural network. To that end, the program code can read metadata in the data provided from the ultrasound machine to the computing device that indicates the data is ultrasound data, e.g., image data. Thus, the program code can enable a neural network for operation on the computing device based on the computing device's resources and the ultrasound data. For example, the ultrasound application on a tablet can determine an input rate to provide image data to the neural network that results in inferences made by the neural network in real time or near real time (i.e., with little or no perceptible delay to the user). Conversely, if the frame rate to the neural network configured for operation on the computing device were increased, the neural network could incur a processing latency that results in an unacceptable perceivable delay to the user.

Returning to FIG. 4, once the program code has implemented the neural network, the program code obtains and provides to the neural network one or more ultrasound images from the ultrasound machine (430). For at least one of the ultrasound images, the neural network applies a machine learning algorithm such as a trained classifier and generates an inference (440). The inference may include a confidence level for the inference. The program code analyzes the inferences with an additional neural network and/or statistical signal processing algorithms (450). Based on results of the analysis, the neural network is reconfigured to generate better inferences (460). For example, better inferences can include inferences with higher confidence levels. For example, the program code executing on the computing device can determine misclassifications in the inferences of the neural network, variances in confidence levels that exceed a threshold confidence level, etc., and based on these determinations, the program code reconfigures the neural network, such as by enabling longer filters, different filter coefficients, etc. In one example, the program code of the neural network reconfigures itself to reconfigure the neural network, so that the neural network is self-configuring. Additionally, or alternatively, program code executed by a processor system of the computing device that is separate from the program code of the neural network can reconfigure the neural network.

FIG. 5 illustrates an example of a workflow 500 for configuring a neural network and implementing the neural network on a computing device (e.g., FIG. 1, computing device 110, other computing device 180, and/or additional computing devices 150). In this example, the computing device is communicatively coupled via a computing network to an ultrasound machine configured to generate the ultrasound data. Referring to the workflow 500, program code executing on one or more processors of a computing device identifies a neural network for implementation on the computing device to generate, based on ultrasound data, inferences (510). The inferences can include confidence levels for the inferences. The program code implements the neural network on the computing device (520). The program code obtains ultrasound data including images from the ultrasound machine (530). The program code configures the neural network to generate an inference for at least one image of the images (540). In some examples, the inference for the at least one image includes a confidence level for the inference. In some examples, the program code configures the neural network to generate an inference for each image of the images. The program code determines, for the at least one image, an accuracy of the inference (550). As aforementioned, the inference can include a confidence level and the program code can also configure the neural network to generate an inference for each image of the images. The program code automatically reconfigures the neural network based on determining that the accuracy should be increased (560). As used herein, the term automatically refers to the program code taking an action without user intervention/input.

Figure 6:
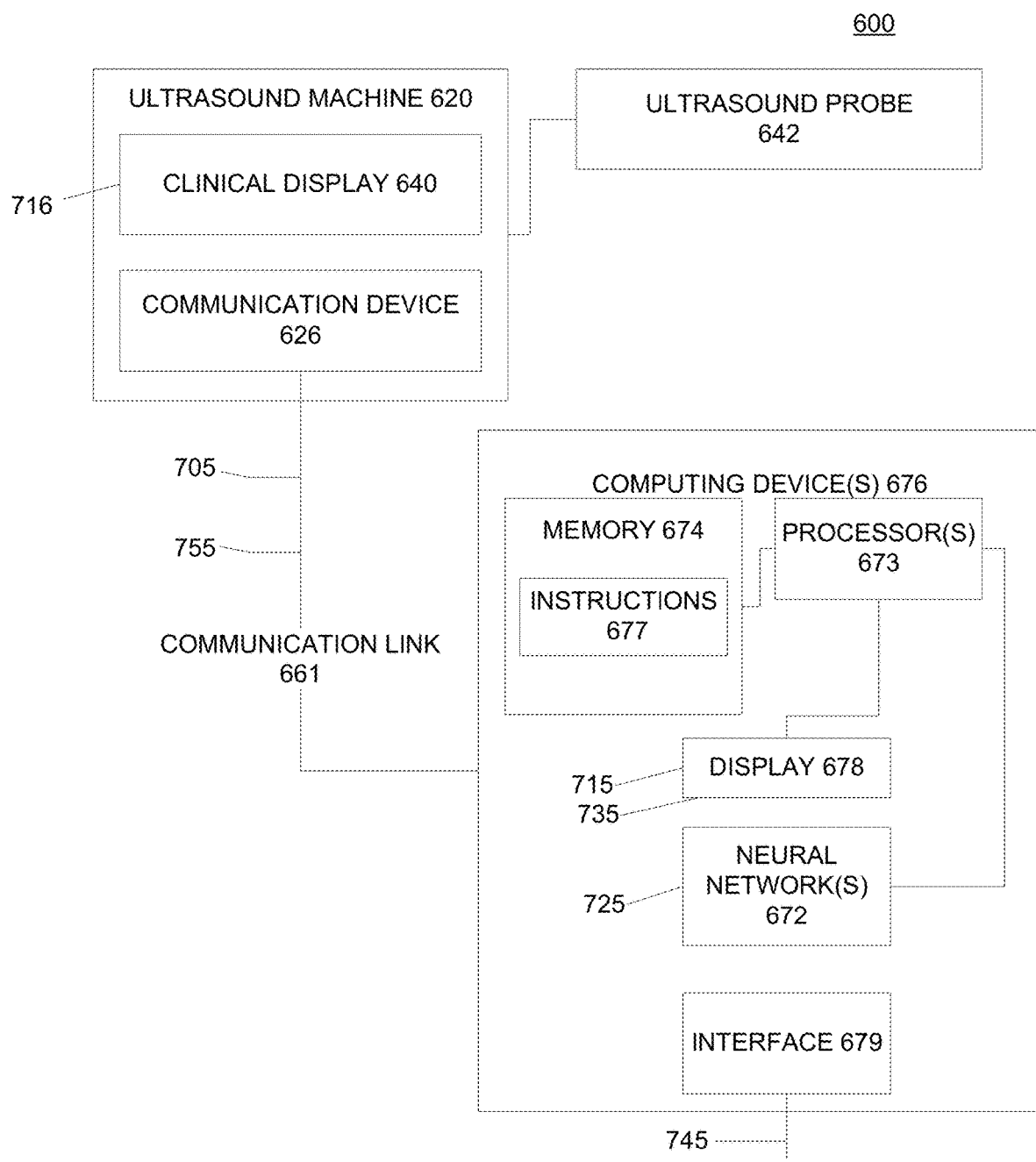
FIG. 6 depicts an example of a combination of an ultrasound system into which aspects of some embodiments of the present invention have been implemented and a workflow, which is depicted in FIG. 7, through the ultrasound system when program instructions execute aspects of the methods described herein.
Figure 7:
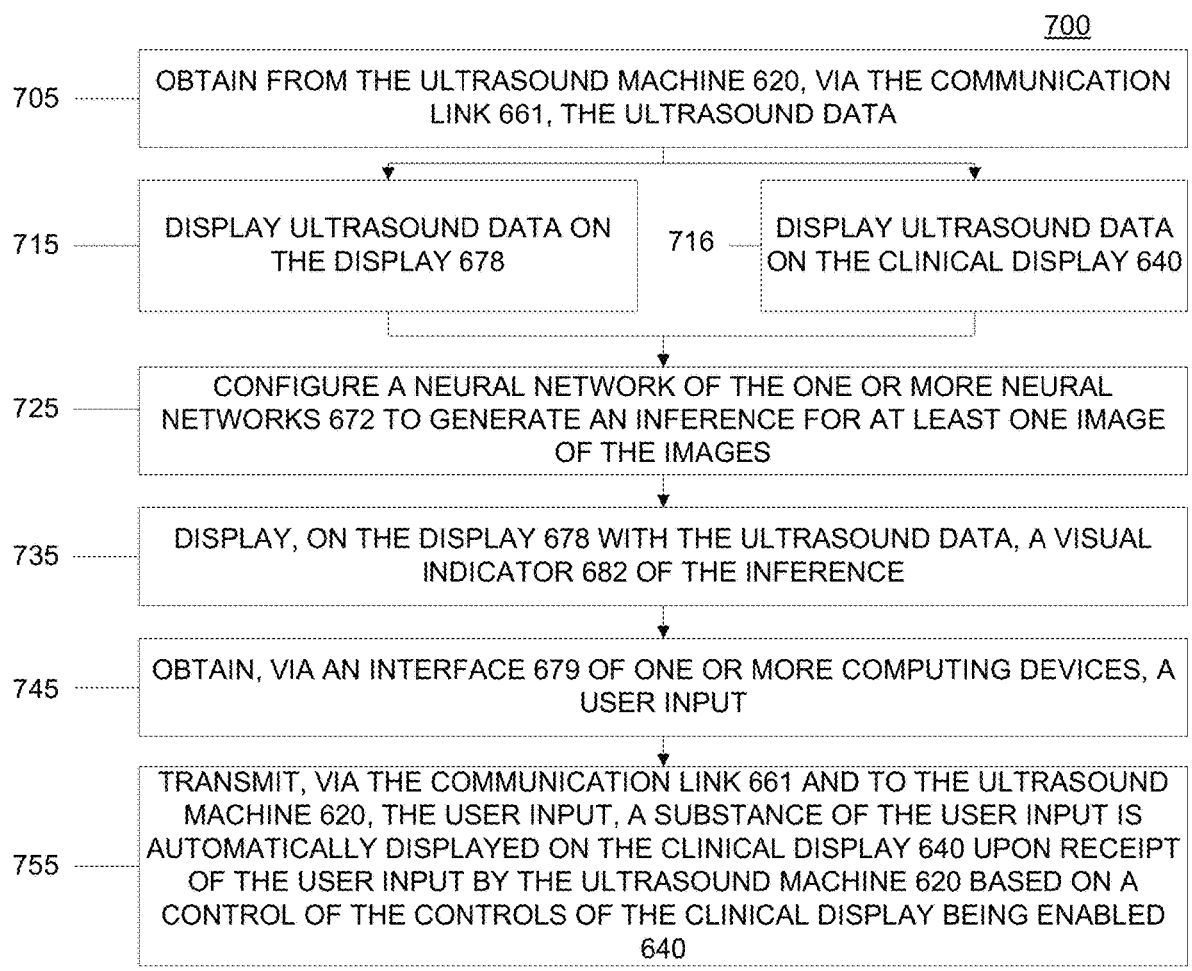
FIG. 7 depicts the example of the workflow which is referenced in FIG. 6.

FIG. 6 is a diagram of various elements of an ultrasound system 600 configured to perform aspects of the processes described herein. FIG. 6 includes various references to FIG. 7, which is an example of a workflow 700. The references from FIG. 7 that are illustrated in FIG. 6 illustrate the interactions of the elements of the ultrasound system 600 within the workflow 700. FIG. 7 also includes references to the elements of the ultrasound system 600 of FIG. 6.

FIG. 6 illustrates both elements of the ultrasound system 600 and interactions (e.g., communications, transmissions, etc.) between the elements. In the ultrasound system, various data is transmitted between different elements.

The ultrasound system 600 includes an ultrasound machine 620 which has a clinical display 640. The clinical display 640 is configured to display ultrasound data including images from an ultrasound probe 642 that is communicatively coupled to the ultrasound machine 620. The ultrasound machine 620 includes a communication device 626 to transmit the ultrasound data to one or more computing devices 676 (e.g., FIG. 1, computing device 110, other computing device 180, and/or additional computing devices 150) via a communication link 661 (e.g., FIG. 1, communications network 160). For ease of illustration, the one or more computing devices 676 are illustrated as a single entity. The communication link 661 can be wired and/or wireless, bidirectional, etc. and couples the communication device 626 of the ultrasound machine 620 to the one or more computing devices 676.

Each of the computing devices 676 in the ultrasound system 600 includes a memory 674, one or more processors 673 in communication with the memory 674, and one or more neural networks 672 accessible to one or more processors 673, and a display 678 in communication with the one or more processors 673. Each computing device 676 also includes program instructions 677 stored on the memory 674 that when executed by the one or more processors 673 cause the one or more processors 673 to perform various activities. For example, the program instructions 677 (when executed) can obtain from the ultrasound machine 620, via the communication link 661, the ultrasound data (705). The program instructions 677 can display the ultrasound data on the display 678 (715), concurrently with displaying the ultrasound data on the clinical display 640 (716). The program instructions 677 configure a neural network of the one or more neural networks 672 to generate an inference for at least one image of the images (725). The inference can include a confidence level and, in some examples, the program instructions 677 configure the neural network to generate inferences for each image of the images. The program instructions 677 can display, on the display 678 with the ultrasound data, a visual indicator of the inference (735). The program instructions 677 obtain, via an interface 679 of the one or more computing devices, a user input (745). The program instructions 677 transmit, via the communication link 661 and to the ultrasound machine 620, the user input, a substance of the user input being automatically displayed on the clinical display 640 upon receipt of the user input by the ultrasound machine 620 based on a control of the controls of the clinical display being enabled 640 (755).

The ultrasound system 600 communicates redundant frames that include coded ultrasound data to facilitate real-time displays of ultrasound data in both the clinical display 640 and in the displays 678 of the computing devices 676. Program code executing on the computing devices 676 can determine which frames received from the ultrasound machine 620 are redundant frames by reading a mark inserted by the program code of the ultrasound machine 620. This program code of the ultrasound machine 620 can insert this mark in file locations including but not limited to, a header or metadata of the frames. When the program code of the computing devices 676 identify one of the redundant frames, rather than displaying the redundant frame as ultrasound image data and/or processing the image data with a neural network 672, the program code of the computing devices 676 can pass the redundant frame to a decoder module of the ultrasound application included in instructions 677. The program code of the decoder module can determine the type of code applied to the redundant frame and decode the ultrasound data from the redundant frame using a decoder (e.g., a QR decoder). In some examples, the program code of a computing device 676 displays the decoded data in an interface 679 of the computing device 676 (e.g., in a sidebar of a user interface that displays parameters of the ultrasound examination communicated via the encoded ultrasound data, such as a gain, angle, system or probe identification number, operator identification number, preset value, and the like). Thus, in this example, the program code of the computing devices 676 displays information that may or may not be displayed on the clinical display 640 of the ultrasound machine 620.

Figure 8:
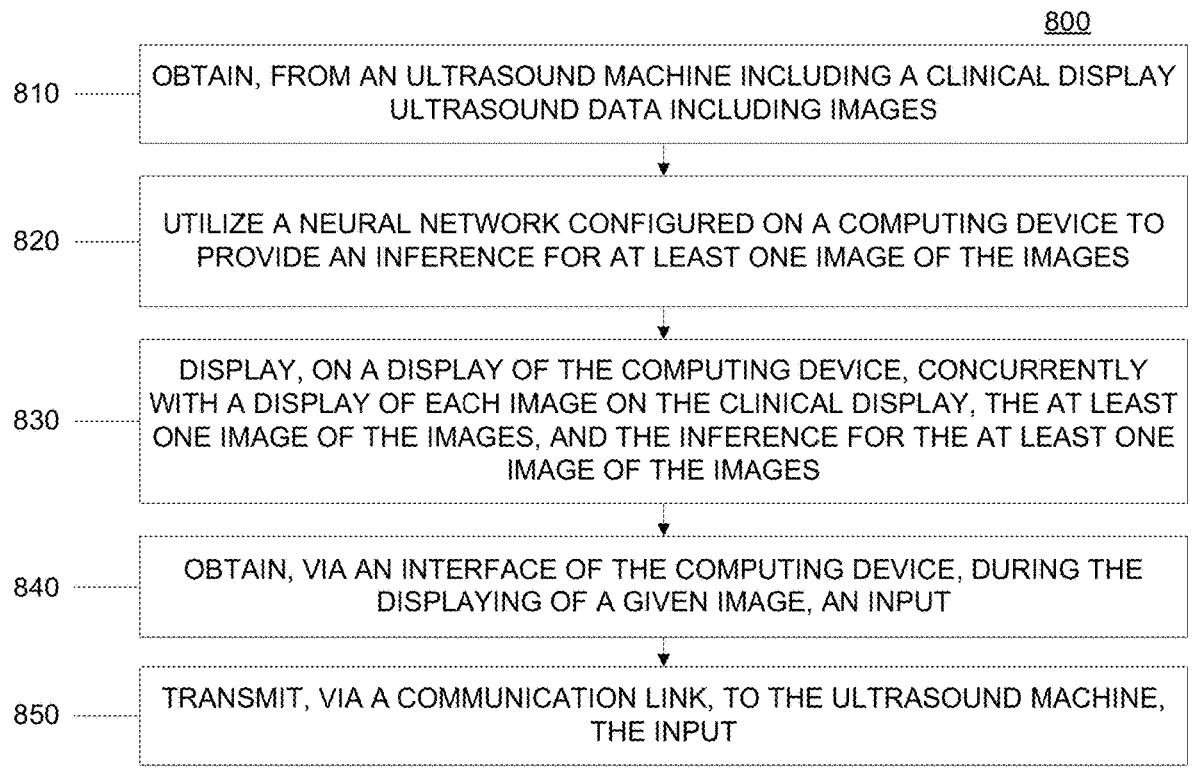
FIG. 8 depicts an example of a workflow for implementing a neural network in some embodiments of the present invention.

FIG. 8 illustrates an example of a workflow 800 that includes various aspects of some embodiments of the present invention. Specifically, the workflow 800 can be performed according to instructions that are executed by a processors. In this example, a computer readable storage medium, readable by one or more processors of a computing device in a computing environment, which includes an ultrasound system, stores computer instructions. In this example, the ultrasound machine is communicatively coupled to the one or more processors. When executed by the one or more processors, the computer instructions obtain from an ultrasound machine that includes a clinical display, ultrasound data including images (810). The instructions, when executed, utilize a neural network configured on the computing device to provide an inference for at least one image of the images (820). Each inference can include a confidence level. The instructions, when executed, display, on a display of the computing device, concurrently with a display of the at least one image on the clinical display, the inference for the at least one image of the images (830). As aforementioned, the inference can include a confidence level. The instructions obtain, via an interface of the computing device, during the displaying of a given image, an input (840). The instructions transmit, via the communication link, to the ultrasound machine, the input (850). The ultrasound machine can effect a change based on obtaining the input, which can include, but is not limited to: a visual change to a display of the given image on the clinical display and/or a change to a setting of an ultrasound probe communicatively coupled to the ultrasound machine.

In some examples herein, a method implemented by a computing device includes program code executing on one or more processors of the computing device identifying a neural network for implementation on the computing device. This neural network, when implemented, generates, based on ultrasound data, inferences. In this example, the computing device is communicatively coupled via a computing network to an ultrasound machine configured to generate the ultrasound data. The program code obtains the ultrasound data including images from the ultrasound machine. The program code implements the neural network on the computing device. To implement the neural network, the program code configures the neural network to generate an inference for at least one image of the images. The program code determines, for the at least one image, an accuracy of the inference. The program code automatically reconfigures the neural network to increase the accuracy based on the program code determining the accuracy.

In some examples of the method described herein, the inferences comprise confidence levels for the inferences.

In some examples of the method described herein, the program code identifying the neural network includes the program code identifying an artificial intelligence (AI) instruction set for use in the implementing the neural network on the computing device. The program code identifies the AI instruction set by determining if the computing device includes the AI instruction set. The program code selects the AI instruction set from the group consisting of: a native AI instruction set and an AI instruction set from an application programming interface (API) supported by the computing device. Based on determining that the computing device includes the AI instruction set, the program code configures the neural network utilizing the AI instruction set.

In some examples of the method described herein, the program code determines if the computing device includes the AI instruction set by querying at least one element of the computing device selected from the group consisting of: a configuration file, an operating system, a device identifier, and a resource manager.

In some examples of the method described herein, the program code identifies the neural network by identifying an artificial intelligence (AI) instruction set for use in the implementing the neural network on the computing device. To identify the AI instruction set including, the program code determines if the computing device includes the AI instruction set. The program code selected the AI instruction set from the group consisting of: a native AI instruction set and an AI instruction set from an application programming interface (API) supported by the computing device. Based on determining that the computing device does not include the AI instruction set, the program code enables a neural network of an ultrasound application executing on the computing device to generate the inference and for at least one image of the images.

In some examples of the method described herein, the program code identifies the neural network by querying the computing device to determine hardware capabilities of the computing device. Based on the hardware capabilities of the computing device, the program code identifies, from a central repository communicatively coupled to the computing device, a neural network model to run on the computing device. The program code imports, from the central repository, the neural network of the neural network model.

In some examples of the method described herein, the ultrasound machine includes the central repository.

In some examples of the method described herein, the program code displays, in a user interface of the computing device, for a given image of the images, a visual representation of the inference for the given image and the given image.

In some examples of the method described herein, the program code obtains, via the user interface of the computing device, a user input. The program code instructs displaying of the user input on an interface of the ultrasound machine.

In some examples of the method described herein, the program code obtains, via the user interface of the computing device, a user input. The program code instructs automatically adjusting one or more settings of the ultrasound machine, based on the user input.

In some examples of the method described herein, the program code obtaining the ultrasound data includes: the program code obtaining the ultrasound data including encoded data; and the program code decoding the encoded data.

In some examples of the method described herein, a method to encode the ultrasound data is selected from the group consisting of: encoding the ultrasound data in an image of decodable indicia, modulating a property of a carrier signal according to the ultrasound data, and modulating a logo to include the encoded data.

In some examples of the method described herein, the communication link supports transfers of the ultrasound data at a frame rate greater than a rate at which the ultrasound machine generates the images. In some examples, the program code obtaining the ultrasound data includes obtaining indications of redundant frames in frames comprising the images, and the program code generating the inference for at least one image of the images is based on the frames without the indications and not the redundant frames.

Some examples of the system described herein include an ultrasound system that comprises an ultrasound machine. The ultrasound machine includes a clinical display including controls. The clinical display is configured to display ultrasound data including images, the ultrasound data obtained from an ultrasound probe communicatively coupled to the ultrasound machine. The ultrasound machine also includes a communication device to transmit the ultrasound data to one or more computing devices via a communication link. The communication link couples the communication device of the ultrasound machine to the one or more computing devices. The ultrasound system also includes the one or more computing devices. Each device comprises a memory, one or more neural networks accessible to one or more processors, the one or more processors in communication with the memory; a display in communication with the one or more processors, and program instructions stored on the memory that when executed by the one or more processors cause the one or more processors to obtain, from the ultrasound machine, via the communication link, the ultrasound data. The program instructions, when executed, display the ultrasound data on the display, concurrently with displaying the ultrasound data on the clinical display. The program instructions, when executed, configure a neural network of the one or more neural networks to generate an inference for at least one image of the images. The program instructions, when executed, display, on the display with the ultrasound data, a visual indicator of the inference. The program instructions, when executed, obtain, via an interface of the one or more computing devices, a user input. The program instructions, when executed, transmit, via the communication link and to the ultrasound machine, the user input, a substance of the user input being automatically displayed on the clinical display upon receipt of the user input by the ultrasound machine based on a control of the controls of the clinical display being enabled.

In some examples of the system described herein, the inference comprises a confidence level for the at least one image of the images.

In some examples of the system described herein, upon the used input being obtained, the ultrasound machine automatically re-configures at least one setting of the ultrasound probe.

In some examples of the system described herein, at least one computing device of the one or more computing devices includes a native AI instruction set. The program instructions, when executed by the one or more processors, further cause the one or more processors to configure the one or more neural networks of the at least one computing device based on the native AI instruction set.

In some examples of the system described herein, at least one computing device of the one or more computing devices supports an API including an AI instruction set The one or more neural networks of the at least one computing device is configured based on the AI instruction set.

In some examples of the system described herein, at least one computing device of the one or more computing devices includes an ultrasound application. The ultrasound application includes the one or more neural networks of the at least one computing device.

In some examples of the system described herein, the communication device encodes the ultrasound data before transmitting the ultrasound data to the one or more computing devices, and wherein the one or more computing devices further include a decoder configured to decode the ultrasound data.

In some examples of the system described herein, the substance of the user input includes editorial changes to an image displayed on the display. The program instructions, when executed by the one or more processors, further cause the one or more processors to: automatically apply the editorial changes to the image displayed on the clinical display responsive to the user input being obtained via the interface of the one or more computing devices.

In some examples of the computer program product disclosed herein, the computer program product includes a computer readable storage medium readable by one or more processors of a computing device in a computing environment comprising an ultrasound system, the computer readable storage medium storing instructions that when executed by the one or more processors cause the one or more processors to: obtain, from an ultrasound machine including a clinical display. The ultrasound machine is communicatively coupled to the one or more processors, ultrasound data including images. The instructions, when executed, utilize a neural network configured on the computing device to provide an inference for at least one image of the images. The instructions, when executed, display, on a display of the computing device, concurrently with a display of the at least one image on the clinical display, the at least one image of the images and the inference for the at least one image of the images. The instructions, when executed, obtain, via an interface of the computing device, during the displaying of the at least one image, an input. The instructions, when executed, transmit, via the communication link, to the ultrasound machine, the input, wherein the ultrasound machine effects a change based on obtaining the input.

In some examples of the computer program product disclosed herein, the change is selected from the group consisting of: a visual change to a display of the at least one image on the clinical display and a change to a setting of an ultrasound probe communicatively coupled to the ultrasound machine.

Figure 9:
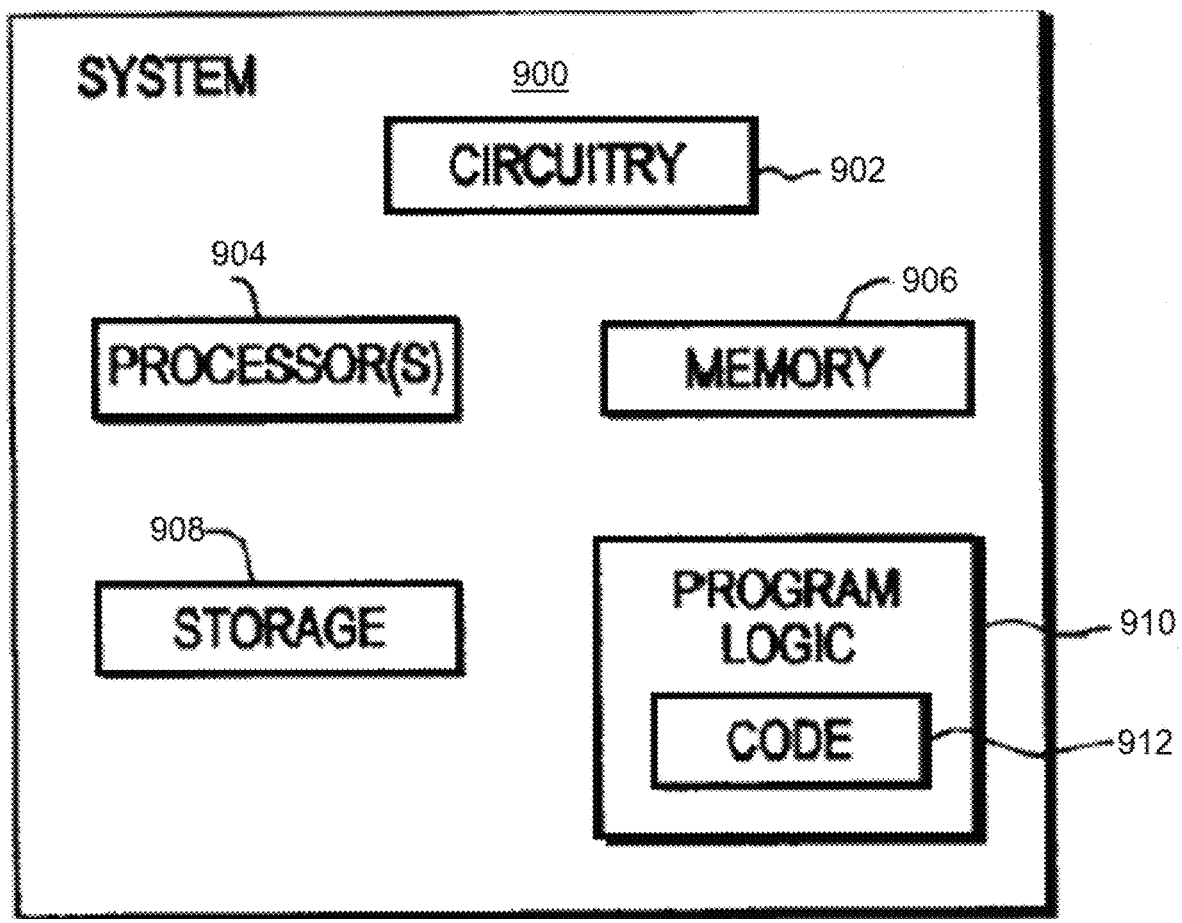
FIG. 9 depicts a computer system configured to perform an aspect of an embodiment of the present invention.

FIG. 9 illustrates a block diagram of a resource 900 in computer system, such as, which is part of the technical architecture of certain embodiments of the technique. The resource 900 can include computing device 110 (FIG. 1), other computing device 180 (FIG. 1), and/or additional computing devices 150 (FIG. 1). The resource 900 may include a circuitry 902 that may in certain embodiments include a microprocessor 904. The computer system 900 may also include a memory 906 (e.g., a volatile memory device), and storage 908. The storage 908 may include a non-volatile memory device (e.g., EEPROM, ROM, PROM, RAM, DRAM, SRAM, flash, firmware, programmable logic, etc.), magnetic disk drive, optical disk drive, tape drive, etc. The storage 908 may comprise an internal storage device, an attached storage device and/or a network accessible storage device. The system 900 may include a program logic 910 including code 912 that may be loaded into the memory 906 and executed by the microprocessor 904 or circuitry 902.

In certain embodiments, the program logic 910 including code 912 may be stored in the storage 908, or memory 906. In certain other embodiments, the program logic 910 may be implemented in the circuitry 902. Therefore, while FIG. 9 shows the program logic 910 separately from the other elements, the program logic 910 may be implemented in the memory 906 and/or the circuitry 902. The program logic 910 may include the program code discussed in this disclosure that facilitates the reconfiguration of elements of various computer networks, including those in various figures.

Figure 10:
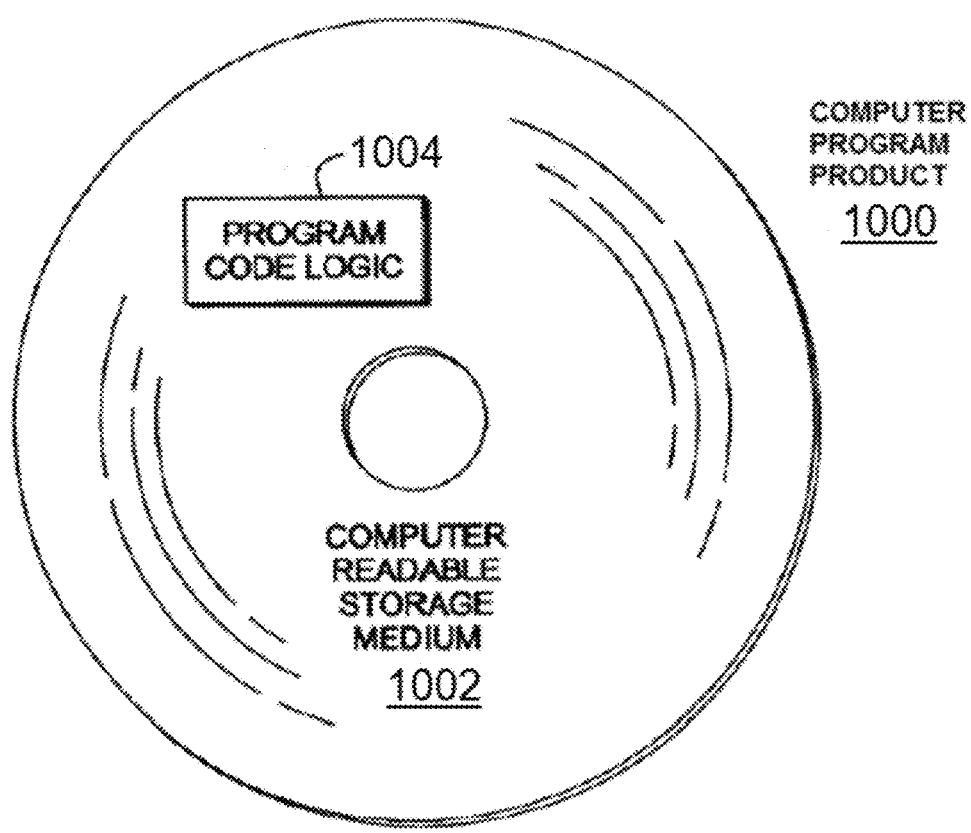
FIG. 10 depicts a computer program product incorporating one or more aspects of the present invention.

Using the processing resources of a resource 900 to execute software, computer-readable code or instructions, does not limit where this code can be stored. Referring to FIG. 10, in one example, a computer program product 1000 includes, for instance, one or more non-transitory computer readable storage media 1002 to store computer readable program code means or logic 1004 thereon to provide and facilitate one or more aspects of the technique.

As will be appreciated by one skilled in the art, aspects of the technique may be embodied as a system, method or computer program product. Accordingly, aspects of the technique may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the technique may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus, or device. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electro-magnetic, optical or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the technique may be written in any combination of one or more programming languages, including an object-oriented programming language, such as Java, Smalltalk, C++ or the like, and conventional procedural programming languages, such as the "C" programming language, PHP, ASP, assembler or similar programming languages, as well as functional programming languages and languages for technical computing (e.g., Python, Matlab). The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). Furthermore, more than one computer can be used for implementing the program code, including, but not limited to, one or more resources in a cloud computing environment.

Aspects of the technique are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions, also referred to as software and/or program code, may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the technique. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In addition to the above, one or more aspects of the technique may be provided, offered, deployed, managed, serviced, etc. by a service provider who offers management of customer environments. For instance, the service provider can create, maintain, support, etc. computer code and/or a computer infrastructure that performs one or more aspects of the technique for one or more customers. In return, the service provider may receive payment from the customer under a subscription and/or fee agreement, as examples. Additionally, or alternatively, the service provider may receive payment from the sale of advertising content to one or more third parties.

In one aspect of the technique, an application may be deployed for performing one or more aspects of the technique. As one example, the deploying of an application comprises providing computer infrastructure operable to perform one or more aspects of the technique.

As a further aspect of the technique, a computing infrastructure may be deployed comprising integrating computer readable code into a computing system, in which the code in combination with the computing system is capable of performing one or more aspects of the technique.

As yet a further aspect of the technique, a process for integrating computing infrastructure comprising integrating computer readable code into a computer system may be provided. The computer system comprises a computer readable medium, in which the computer medium comprises one or more aspects of the technique. The code in combination with the computer system is capable of performing one or more aspects of the technique.

Further, other types of computing environments can benefit from one or more aspects of the technique. As an example, an environment may include an emulator (e.g., software or other emulation mechanisms), in which a particular architecture (including, for instance, instruction execution, architected functions, such as address translation, and architected registers) or a subset thereof is emulated (e.g., on a native computer system having a processor and memory). In such an environment, one or more emulation functions of the emulator can implement one or more aspects of the technique, even though a computer executing the emulator may have a different architecture than the capabilities being emulated. As one example, in emulation mode, the specific instruction or operation being emulated is decoded, and an appropriate emulation function is built to implement the individual instruction or operation.

In an emulation environment, a host computer includes, for instance, a memory to store instructions and data; an instruction fetch unit to fetch instructions from memory and to optionally, provide local buffering for the fetched instruction; an instruction decode unit to receive the fetched instructions and to determine the type of instructions that have been fetched; and an instruction execution unit to execute the instructions. Execution may include loading data into a register from memory; storing data back to memory from a register; or performing some type of arithmetic or logical operation, as determined by the decode unit. In one example, each unit is implemented in software. For instance, the operations being performed by the units are implemented as one or more subroutines within emulator software.

Further, a data processor system suitable for storing and/or executing program code is usable that includes at least one processor coupled directly or indirectly to memory elements through a system bus. The memory elements include, for instance, local memory employed during actual execution of the program code, bulk storage, and cache memory which provide temporary storage of at least some program code in order to reduce the number of times code must be retrieved from bulk storage during execution.

Input/Output or I/O devices (including, but not limited to, keyboards, displays, pointing devices, DASD, tape, CDs, DVDs, thumb drives and other memory media, etc.) can be coupled to the system either directly or through intervening I/O controllers. Network adapters may also be coupled to the system to enable the data processor system to become coupled to other data processing systems or remote printers or storage devices through intervening private or public networks. Modems, cable modems, and Ethernet cards are just a few of the available types of network adapters.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components and/or groups thereof.

The corresponding structures, materials, acts, and equivalents of all means or steps plus function elements in the descriptions below, if any, are intended to include any structure, material, or act for performing the function in combination with other elements as specifically noted. The description of the technique has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular uses contemplated.

What is claimed is:

1. A method implemented by a computing device, the method comprising:

identifying, by one or more processors of the computing device, a neural network for implementation on the computing device to generate, based on ultrasound data, inferences, the computing device being communicatively coupled via a computing network to an ultrasound machine configured to generate the ultrasound data;

obtaining, by the one or more processors, the ultrasound data including images from the ultrasound machine;

implementing, by the one or more processors, the neural network on the computing device, the implementing including configuring the neural network to generate an inference for at least one image of the images;

determining, for the at least one image, an accuracy of the inference; and automatically reconfiguring, by the one or more processors, the neural network to increase the accuracy based on the determining the accuracy.

2. The method of claim 1, wherein the inferences comprise confidence levels for the inferences.

3. The method of claim 1, wherein the identifying the neural network includes:

identifying, by the one or more processors, an artificial intelligence (AI) instruction set for use in the implementing the neural network on the computing device, the identifying the AI instruction set including:

determining, by the one or more processors, if the computing device includes the AI instruction set, wherein the AI instruction set is selected from the group consisting of: a native AI instruction set and an AI instruction set from an application programming interface (API) supported by the computing device; and based on determining that the computing device includes the AI instruction set, configuring, by the one or more processors, the neural network utilizing the AI instruction set.

4. The method of claim 3, wherein the determining if the computing device includes the AI instruction set includes:

querying, by the one or more processors, at least one element of the computing device selected from the group consisting of: a configuration file, an operating system, a device identifier, and a resource manager.

5. The method of claim 1, wherein the identifying the neural network includes:

identifying, by the one or more processors, an artificial intelligence (AI) instruction set for use in the implementing the neural network on the computing device, the identifying the AI instruction set including:

determining, by the one or more processors, if the computing device includes the AI instruction set, wherein the AI instruction set is selected from the group consisting of: a native AI instruction set and an AI instruction set from an application programming interface (API) supported by the computing device; and based on determining that the computing device does not include the AI instruction set, enabling, by the one or more processors, a neural network of an ultrasound application executing on the computing device to generate the inference and for at least one image of the images.

6. The method of claim 1, wherein the identifying the neural network includes:

querying, by the one or more processors, the computing device to determine hardware capabilities of the computing device;

based on the hardware capabilities of the computing device, identifying, by the one or more processors, from a central repository communicatively coupled to the computing device, a neural network model to run on the computing device; and importing, from the central repository, the neural network of the neural network model.

7. The method of claim 6, wherein the ultrasound machine includes the central repository.

8. The method of claim 7, further comprising:

displaying, by the one or more processors, in a user interface of the computing device, for a given image of the images, a visual representation of the inference for the given image and the given image.

9. The method of claim 8, further comprising:

obtaining, by the one or more processors, via the user interface of the computing device, a user input; and instructing, by the one or more processors, displaying of the user input on an interface of the ultrasound machine.

10. The method of claim 8, further comprising:

obtaining, by the one or more processors, via the user interface of the computing device, a user input; and instructing, by the one or more processors, automatically adjusting one or more settings of the ultrasound machine, based on the user input.

11. The method of claim 1, wherein the obtaining the ultrasound data includes:

obtaining, by the one or more processors, the ultrasound data including encoded data; and decoding, by the one or more processors, the encoded data.

12. The method of claim 11, wherein a method to encode the ultrasound data is selected from the group consisting of: encoding the ultrasound data in an image of decodable indicia, modulating a property of a carrier signal according to the ultrasound data, and modulating a logo to include the encoded data.

13. The method of claim 8, wherein the communication link supports transfers of the ultrasound data at a frame rate greater than a rate at which the ultrasound machine generates the images, wherein the obtaining the ultrasound data includes obtaining indications of redundant frames in frames comprising the images, and wherein the generating the inference for at least one image of the images is based on the frames without the indications and not the redundant frames.

* * * * *